(12) United States Patent
Rogawski et al.

(10) Patent No.: US 11,510,929 B2
(45) Date of Patent: Nov. 29, 2022

(54) MITIGATION OF EPILEPTIC SEIZURES BY COMBINATION THERAPY USING BENZODIAZEPINES AND NEUROSTEROIDS

(71) Applicant: The Regents of the University of California, Oakland, CA (US)

(72) Inventors: Michael A. Rogawski, Sacramento, CA (US); Isaac N. Pessah, Davis, CA (US); Zhengyu Cao, Woodland, CA (US); Pamela J. Lein, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/544,480

(22) Filed: Aug. 19, 2019

(65) Prior Publication Data

US 2020/0215078 A1 Jul. 9, 2020

Related U.S. Application Data

(63) Continuation of application No. 15/649,460, filed on Jul. 13, 2017, now Pat. No. 10,426,786, which is a continuation of application No. 13/964,922, filed on Aug. 12, 2013, now abandoned.

(60) Provisional application No. 61/798,094, filed on Mar. 15, 2013, provisional application No. 61/682,745, filed on Aug. 13, 2012.

(51) Int. Cl.
| | |
|---|---|
| *A61K 31/57* | (2006.01) |
| *A61K 31/5517* | (2006.01) |
| *A61K 31/5513* | (2006.01) |
| *A61K 31/439* | (2006.01) |
| *A61P 25/08* | (2006.01) |
| *A61K 45/06* | (2006.01) |

(52) U.S. Cl.
CPC ............ *A61K 31/57* (2013.01); *A61K 31/439* (2013.01); *A61K 31/5513* (2013.01); *A61K 31/5517* (2013.01); *A61K 45/06* (2013.01); *A61P 25/08* (2018.01)

(58) Field of Classification Search
CPC .... A61K 9/007; A61K 31/57; A61K 31/5513; A61P 25/08
See application file for complete search history.

(56) References Cited

U.S. PATENT DOCUMENTS

| | | |
|---|---|---|
| 3,865,939 A | 2/1975 | Jandacek |
| 6,455,516 B1 | 9/2002 | Backstrom et al. |
| 7,060,255 B2 | 6/2006 | Rabinowitz et al. |
| 7,090,830 B2 | 8/2006 | Hale et al. |
| 9,084,797 B2 | 7/2015 | Caufriez et al. |
| 10,172,870 B2 | 1/2019 | Reddy |
| 2003/0032638 A1 | 2/2003 | Kim et al. |
| 2006/0063707 A1 | 3/2006 | Baudry et al. |
| 2006/0198896 A1 | 9/2006 | Liversidge et al. |
| 2007/0021411 A1 | 1/2007 | Cloyd et al. |
| 2007/0081948 A1 | 4/2007 | Morton |
| 2007/0287931 A1 | 12/2007 | Dilorenzo |
| 2008/0269183 A1 | 10/2008 | Mellon et al. |
| 2009/0162441 A1 | 6/2009 | Bartus et al. |
| 2009/0198145 A1 | 8/2009 | Chow |
| 2010/0136105 A1 | 6/2010 | Chen et al. |
| 2010/0234335 A1 | 9/2010 | Gravanis et al. |
| 2010/0297181 A1 | 11/2010 | Hanada et al. |
| 2010/0316678 A1 | 12/2010 | Goodchild |
| 2011/0054038 A1 | 3/2011 | Glozman |
| 2011/0319386 A1 | 12/2011 | Barlow et al. |
| 2012/0302535 A1 | 11/2012 | Caufriez et al. |
| 2013/0309306 A1 | 11/2013 | Rogawski et al. |
| 2014/0057885 A1 | 2/2014 | Reddy et al. |
| 2014/0343027 A1 | 11/2014 | Rogawski et al. |
| 2015/0158903 A1 | 6/2015 | Upasani et al. |
| 2015/0175651 A1 | 6/2015 | Salituro et al. |
| 2015/0313915 A1 | 11/2015 | Rogawski et al. |

FOREIGN PATENT DOCUMENTS

| | | |
|---|---|---|
| EP | 0 233 849 | 1/1987 |
| WO | WO 2007/062266 | 5/2007 |
| WO | WO 2008/157460 | 12/2008 |
| WO | WO 2010/107815 | 9/2010 |
| WO | WO 2011/088503 | 7/2011 |
| WO | WO 2012/075286 | 6/2012 |
| WO | WO 2013/043985 | 3/2013 |
| WO | WO 2013/112605 | 8/2013 |
| WO | WO 2014/028398 | 2/2014 |

(Continued)

OTHER PUBLICATIONS

Whitlow et al., "Tetramethylenedisulfotetramine: old agent and new terror," Ann. Emerg. Med. 45(6), 609-13. PMID: 15940093. (Year: 2005).*
PCT International Search Report and Written Opinion dated Jan. 13, 2014 issued in PCT/US2013/054562.
Bruun, et al. 2015, "Combined treatment with diazepam and allopregnanolone reverses tetramethylenedisulfotetramine (TETS)-induced calcium dysregulation in cultured neurons and protects TETS-intoxicated mice against lethal seizures." *Neuropharmacology* 95:332-342.

(Continued)

*Primary Examiner* — Theodore R. Howell

(74) *Attorney, Agent, or Firm* — Squire Patton Boggs (US) LLP

(57) ABSTRACT

Provided are compositions comprising a benzodiazepine and a neurosteroid, containing one or both of the benzodiazepine and the neurosteroid in a subtherapeutic dose, and administration of such compositions for mitigation of an epileptic seizure. Further provided are compositions comprising a benzodiazepine, a neurosteroid, and an NMDA blocker, and administration of such compositions for mitigation of an epileptic seizure.

16 Claims, 25 Drawing Sheets

(56) References Cited

FOREIGN PATENT DOCUMENTS

WO    WO 2014/085668      6/2014

OTHER PUBLICATIONS

Cao, et al. 2012, "Tetramethylenedisulfotetramine Alters $Ca^{2+}$ Dynamics in Cultured Hippocampal Neurons: Mitigation by NMDA Receptor Blockade and $GABA_A$ Receptor-Positive Modulation," *Toxicological Sciences* 130(2):362-372.

Dhir, et al. 2012, "Role of neurosteroids in the anticonvulsant activity of midazolam," *British Journal of Pharmacology* 165:2684-2691.

Gasior, et al. 1997, "Anticonvulsant and Behavioral Effects of Neuroactive Steroids Alone and in Conjunction with Diazepam," The American Society for Pharmacology and Experimental Therapeutics 282(2): 543-553.

U.S. Office Action dated Apr. 16, 2015 issued in U.S. Appl. No. 13/885,660.

U.S. Final Office Action dated Nov. 30, 2015 issued in U.S. Appl. No. 13/885,660.

U.S. Restriction Requirement dated Aug. 18, 2015 issued in U.S. Appl. No. 14/345,385.

PCT International Search Report (Declaration of non-establishment of International Search Report) and Written Opinion dated Jun. 15, 2012 issued in PCT/US2011/062888.

PCT International Preliminary Report on Patentability and Written Opinion dated Jun. 13, 2013 issued in PCT/US2011/062888.

PCT International Search Report and Written Opinion dated Dec. 27, 2012 issued in PCT/US2012/056509.

PCT International Preliminary Report on Patentability and Written Opinion dated Apr. 3, 2014 issued in PCT/US2012/056509.

PCT International Preliminary Report on Patentability and Written Opinion dated Jun. 18, 2015 issued in PCT/US2013/054562.

PCT International Search Report and Written Opinion dated Mar. 17, 2014 issued in PCT/US2013/072351.

PCT International Preliminary Report on Patentability and Written Opinion dated Jun. 11, 2015 issued in PCT/US2013/072351.

Bancaud, Jean; Henriksen, Olaf; Rubio-Donnadieu, Francisco; Seino (Shizuoka), Masakatsu; Dreifuss, Fritz E.; Penry, J. Kiffin; (From the Commission on Classification and Terminology of the International League Against Epilepsy) (Aug. 1981) "Proposal for Revised Clinical and Electroencephalographic Classification of Epileptic Seizures," *Epilepsia*, 22:489-501.

Bobb et al. "Allopregnanolone to Treat Refractory Status Epilepticus," presented at *American Clinical Neurophysiology Society (ACNS) Annual Meeting & Courses*, The Westin Peachtree Plaza, Atlanta, Georgia, (Feb. 4-9, 2014) Abstract S26.

Broomall et al. (Dec. 2014) "Pediatric Super-Refractory Status Epilipticus Treated with Allopregnanolone," *Ann. Neurol*, 76:911-915.

Dhir et al. (Jan. 2011) "Seizure Protection by Intrapulmonary Delivery of Propofol Hemisuccinate," *The Journal of Pharmacology and Experimental Therapeutics*, 336(1):215-222.

Dhir et al. (2013) "Seizure protection by intrapulmonary delivery of midazolam in mice," *Neuropharmacology*, 73:425e431.

Galvin et al. (1987) "Midazolam: an effective intravenous agent for seizure control," *Archives of Emergency Medicine*, 4:169-172.

Gul et al. (2006) "Sterols and the phytosterol content in oilseed rape (*Brassica napus* L.)," *Journal of Cell and Molecular Biology*, 5:71-79.

Hanley et al. (1998) "Use of Midazolam in the treatment of refractory status epilepticus," *Clinical Therapeutics*, 20(6): 1093-1105.

Haut, Sheryl R. (2006) "Seizure clustering," *Epilepsy & Behavior*, 8:50-55.

Kanto (May/Jun. 1985) Midazolam: The First Water-soluble Benzodiazepine Pharmacology, Pharmacokinetics and Efficacy in Insomnia and Anesthesia, *Pharmacotherapy*, 5(3): 138-155.

Lallement, G. et al. (1998) "Medical management of organophosphate-induced seizures" *Journal of Physiology* (Paris), vol. 92, Nos. 5-6, pp. 369-373.

Martini et al. (2000) "Nasal and pulmonary drug delivery systems," *Exp. Opin. Ther. Patents*, 10(3):315-323.

McDonough, J. H. et al. (2010) "Time-dependent reduction in the anticonvulsant effectiveness of diazepam against soman-induced seizures in guinea pigs" *Drug and Chemical Toxicology*, vol. 33, No. 3, pp. 279-283.

Nanjwade et al. (Sep.-Oct. 2011) "Pulmonary Drug Delivery: Novel Pharmaceutical Technologies Breathe New Life into the Lungs," *PDA JPharm Sci and Tech*, [Downloaded from journal.pda.org on Oct. 8, 2015] 65:513-534.

Oka et al. (2006) "A Reliable Method for Intratracheal Instillation of Materials to the Entire Lung in Rats," *J Toxicol Pathol*, 19:107-109.

Pires et al. (2009) "Intranasal Drug Delivery: How, Why and What for?" *JPharm Pharmaceut Sci*, 12(3):288-311.

Ramsay, Eugene R., (1993) "Treatment of Status Epilepticus," *Epilepsia*, 34(Suppl. 1):S71-S81.

Reddy, D. S. (Oct. 2011) "Role of anticonvulsant and antiepileptogenic neurosteroids in the pathophysiology and treatment of epilepsy," *Frontiers in Endocrinology*, vol. 2, Article 38, pp. 1-11.

Reddy (Sep. 2013) "SGE-102: a novel therapy for refractory status epilepticus," *Epilepsia*, Abstract, 54 Suppl 6:81-83, 2 pages [retrieved on Sep. 7, 2015 at http://wwvv.ncbi.nlm.nih.gov/pubmed/24001082].

Rogawski et al. (Sep. 2013) "Neuroactive Steroids for the Treatment of Status Epilepticus," *Epilepsia*, Author manuscript; available in PMC Sep. 1, 2014., 54(0 6): 93-98, doi:10.1111/epi.12289.

Sanborn et al. (May 28, 2002) "Identifying and managing adverse environmental health effects: 4. Pesticides," *CMAJ*, 166(11):1431-1436.

Vaitkevicius et al. (2013) "Successful Allopregnanolone Treatment of New Onset Refractory Status Epilepticus (Norse) Syndrome: First in Man Experience", *Epilepsia*, Abstract P29, p. 114.

U.S. Office Action dated Feb. 11, 2016 issued in U.S. Appl. No. 14/345,385.

U.S. Restriction Requirement dated May 9, 2016 issued in U.S. Appl. No. 14/646,886.

European Extended Search Report dated May 2, 2016 issued in Application No. EP 13 85 7993.

Burdock, G.A. (1997) "Encyclopedia of Food Additives and Coloring," *Taylor & Francis*, 3 Volume Set, p. 2412, 4pp.

Frye, C.A. (1995) "The neurosteroid 3-a, 5 a-THP has antiseizure and possible neuroprotective effects in an animal model of epilepsy," *Brain Research*, 696:113-120.

PubChem CID 92786, Allopregnanolone1C211-13402, [Retrieved online on Dec. 7, 2015 at <URL:https:/pubchem.ncbi.nlm.nih.gov/compound/92786#section=Top>], 20 pages.

\* cited by examiner

MITIGATION OF EPILEPTIC SEIZURES BY COMBINATION THERAPY USING BENZODIAZEPINES AND NEUROSTEROIDS

CROSS-REFERENCE TO RELATED APPLICATIONS

This application is a continuation of U.S. application Ser. No. 15/649,460 filed on Jul. 13, 2017, which is a continuation of U.S. application Ser. No. 13/964,922 filed on Aug. 12, 2013, now abandoned, which claims the benefit under 35 U.S.C. § 119(e) of U.S. Provisional Application No. 61/682,745 filed on Aug. 13, 2012, and U.S. Provisional Application No. 61/798,094 filed on Mar. 15, 2013, all of which are hereby incorporated herein by reference in their entireties for all purposes.

STATEMENT OF GOVERNMENTAL SUPPORT

This invention was made with Government support under Grant Nos. AG032119, NS072094, and NS079202 awarded by the National institutes of Health. The Government has certain rights in this invention.

FIELD

Provided are compositions comprising a benzodiazepine and a neurosteroid, containing one or both of the benzodiazepine and the neurosteroid in a subtherapeutic dose, and administration of such compositions for mitigation of an epileptic seizure. Further provided are compositions comprising a benzodiazepine, a neurosteroid, and an NMDA blocker, and administration of such compositions for mitigation of an epileptic seizure.

BACKGROUND

Tetramethylenedisulfotetramine (TETS), commonly called tetramine or TETS, is a highly toxic convulsant with a parenteral LD50 of 0.1-0.3 mg/kg in mice or rats (Haskell and Voss, 1957; Voss et al., 1961; Casida et al., 1976). In adult humans, 7-10 mg is estimated as a lethal dose (Guan et al., 1993) TETS was used as a rodenticide until banned worldwide in the early 1990's (Whitlow et al., 2005. Banks et al., 2012). It is, however, still available illegally, and is responsible for accidental and intentional poisonings, predominantly in China (Croddy, 2004, Wu and Sun, 2004, Zhang et al. 2011), but also in other countries, including the United States (Barrueto et al., 2003). Between 1991 and 2010 over 14,000 cases of TETS intoxication were reported in China with 932 deaths (Li et al., 2011). Extreme toxicity, history of intentional mass poisonings, and the absence of a specific antidote raise concern that TETS is a potential chemical threat agent that could cause mass casualties if released accidentally or intentionally (Whitlow et al., 2005; Jell and Yeung, 2010).

Mild to moderate poisoning with TETS leads to headache and dizziness whereas severe intoxication produces status epilepticus and coma (Whitlow et al., 2005; Li et al., 2011). Animal studies demonstrate that TETS is active as a convulsant when administered orally, parenterally and intraventricularly. Sublethal seizures are not associated with evidence of cellular injury or neurodegeneration although there is delayed transient reactive astrocytosis and microglial activation (Zolkowska et al., 2012).

The primary convulsant mechanism of TETS has been thought to relate to blockade of $GABA_A$ receptors and the seizures induced in animals resemble those produced by other $GABA_A$ receptor antagonists including picrotoxin and pentylenetetrazol. Limited cellular physiological studies and results from $[^{35}S]$t-butylbicyclophosphorothionate binding to brain membranes indicate that TETS inhibits $GABA_A$ receptors with an IC50 in the range of 1 μM (Squires et al, 1983; Esser et al, 1991; Ratra et al., 2001) and it is therefore comparable in potency to picrotoxin as an inhibitor of $GABA_A$ receptors (Squires et al., 1983; Cole and Casida, 1986, Ratra et al, 2001).

Cultured hippocampal neurons display synchronous spontaneous Ca2+ oscillations (Tanaka et al, 1996) that are driven by action potential-dependent synaptic transmission Disruption of Ca2+ oscillations by environmental toxicants has been reported (Soria-Mercado et al., 2009; Cao et al, 2010, Choi et al, 2010, Percira et al., 2010, Cao et al., 2011). Hippocampal neurons also exhibit spontaneous electrical discharges as they form functional neuronal networks. These discharges, as detected in extracellular recordings, consist of infrequent synchronized field potentials, mixed with more frequent desynchronized random action potentials (Cao et al., 2012; Frega et al., 2012). Synchronous Ca2− oscillations and neuronal electrical firing co-occur (Jimbo et al., 1993) and are important in mediating neuronal development and activity dependent dendritic growth (Wayman et al., 2008) Genetic or environmental factors that interfere with neuronal transmission influence the overall neuronal networks activity (Kenet et al., 2007, Meyer et al., 2008; Shafer et al., 2008; Frega et al., 2012; Wayman et al., 2012). For example picrotoxin, a $GABA_A$ receptor antagonist, produces striking changes in network electric activity (Cao et al., 2012; Frega et al., 2012). Diisopropylfluorophosphate, an irreversible inhibitor of cholinesterase has also been shown to elicit status epileptics in rats. Hippocampal neurons dissociated from the brains of diisopropylfluorophosphate exposed rats display significantly higher intracellular Ca2| concentration which appears to be dependent on the N-methy-D-aspartate receptors (Deshpande et al., 2010).

In the present study, using rapid throughput assays we characterized the influence of TETS on the Ca2| dynamics and neuronal firing activity. Inasmuch as TETS induces changes in Ca2· dynamics that are similar to those produced by the $GABA_A$ receptor antagonists picrotoxin and bicuculline, our results support the view that TETS acts as a $GABA_A$ receptor antagonist. Using rapid throughput Ca2· measurement, we identified several agents that reduce or prevent the alterations in Ca2− dynamics induced by TETS, suggesting several treatment strategies for TETS-induced seizures, including the $GABA_A$ receptor positive modulators diazepam and allopregnanolone. In preliminary studies with mice, we confirmed that these two agents do inhibit TETS-induced clonic seizures and progression to tonic seizures and death supporting that measurement of Ca2· dynamics is likely useful for identifying novel targeted interventions for TETS poisoning.

SUMMARY

In one aspect, provided are compositions comprising a benzodiazepine and a neurosteroid. In varying embodiments, the compositions comprise one or both of the benzodiazepine and the neurosteroid in a subtherapeutic dose or amount. In varying embodiments, the compositions further comprise a NMDA receptor antagonist. In some embodiments, the composition is formulated for inhalational, intranasal or intrapulmonary administration. In some embodiments, the composition is formulated for oral or transmucosal delivery. In varying embodiments, the composition is formulated for parenteral delivery. In some embodiments, the parenteral delivery or administration is via a route selected from the group consisting of inhalational, intrapulmonary, intranasal, intramuscular, subcutaneous, transmucosal and intravenous. In some embodiments, the composition is formulated for intramuscular delivery. In some embodiments, the benzodiazepine is an agonist of the benzodiazepine recognition site on $GABA_A$ receptors and stimulates endogenous neurosteroid synthesis. In some embodiments, the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the benzodiazepine is selected from the group consisting of midazolam, lorazepam and diazepam. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the neurosteroid is allopregnanolone. In some embodiments, the composition comprises allopregnanolone and a benzodiazepine selected from the group consisting of midazolam, lorazepam and diazepam. In some embodiments, the neurosteroid is suspended or dissolved in a cyclodextrin (e.g., an α-cyclodextrin, a β-cyclodextrin or a γ-cyclodextrin). In varying embodiments, the neurosteroid is suspended or dissolved in a cyclodextrin selected from the group consisting of hydroxypropyl-β-cyclodextrin, endotoxin controlled β-cyclodextrin sulfobutyl ethers, or cyclodextrin sodium salts (e.g., CAPTISOL®). In some embodiments, the neurosteroid is suspended or dissolved in an edible oil. In some embodiments, the edible oil comprises one or more vegetable oils. In some embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof. In some embodiments, the edible oil is canola oil. In some embodiments, the edible oil comprises one or more nut oils. In some embodiments, the nut oil is selected from the group consisting of almond oil, cashew oil, hazelnut oil, macadamia oil, mongongo nut oil, pecan oil, pine nut oil, pistachio nut oil, walnut oil, and mixtures thereof. In some embodiments, the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine tenocyclidine, methoxydine, tiletamine, xenon, neramexane, cliprodil, etoxadrol, dexoxadrol, WMS 2539, NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13. In some embodiments, the NMDA receptor antagonist is selected from the group consisting of ketamine, dextromethorphan, phencyclidine. CPPene (3-[(R)-2-carboxypiperazin-4-yl]-prop-2-enyl-1-phosphonic acid), selfotel, amantadine dextrorphan, memantine, tiletamine, neramexane, cliprodil, remacemide, aptiganel, 1-Aminocyclopropanecarboxylic acid (ACPC), 7-Chlorokynurenate, DCKA (5,7-dichlorokynurenic acid), kynurenic acid, CP-101,606 (traxoprodil), AZD6765 (lanicemine) and GLYX-13. In some embodiments, the NMDA receptor antagonist is dizocilpine (MK-801). In varying embodiments, the composition comprises a benzodiazepine and a neurosteroid formulated in a cyclodextrin, e.g., for intramuscular, intravenous and/or subcutaneous administration.

In another aspect, provided are methods of preventing or terminating a seizure in a subject in need thereof. In varying embodiments, the methods comprise administration to the subject of an effective amount of a composition as described above and herein. Also provided are methods of accelerating the termination or abortion of an impending seizure in a subject in need thereof. In varying embodiments, the methods comprise administration to the subject of an effective amount of a composition as described above and herein. In some embodiments, the composition is administered via inhalational or intrapulmonary administration. In some embodiments, the composition is not heated prior to administration. In some embodiments, the composition is nebulized. In some embodiments, the nebulized particles are about 3 μm or smaller. In some embodiments, the nebulized particles are about 2-3 μm. In some embodiments, the composition is delivered to the distal alveoli. In some embodiments, the composition is administered orally. In some embodiments, the composition is contained within a soft gel capsule. In some embodiments, the composition is administered parenterally. In some embodiments, the composition is administered via a parenteral route selected from the group consisting of inhalational, intrapulmonary, intranasal, intramuscular, subcutaneous, transmucosal and intravenous. In some embodiments, the composition is administered transmucosally. In varying embodiments, the method comprises co-administering a benzodiazepine and a neurosteroid formulated in a cyclodextrin, e.g., intramuscularly, intravenously and/or subcutaneously.

In a related aspect, methods of preventing or terminating a seizure in a subject in need thereof, comprising administration to the subject of an effective amount of a benzodiazepine and a neurosteroid. In varying embodiments, one or both of the benzodiazepine and the neurosteroid are administered in a subtherapeutic dose. Further are provided methods of accelerating the termination or abortion of an impending seizure in a subject in need thereof. In varying embodiments, the methods comprise administration to the subject of an effective amount of a benzodiazepine and a neurosteroid. In some embodiments, one or both of the benzodiazepine and the neurosteroid are administered in a subtherapeutic dose. In some embodiments, the benzodiazepine and the neurosteroid are co-administered together and/or by the same route of administration. In some embodiments, the benzodiazepine and the neurosteroid are co-administered separately and/or by different routes of administration. In some embodiments, one or both of the benzodiazepine and the neurosteroid are self-administered by the subject. In some embodiments, one or both of the benzodiazepine and the neurosteroid are administered via inhalational or intrapulmonary administration. In some embodiments, one or both of the benzodiazepine and the neurosteroid are not heated prior to administration. In some embodiments, one or both of the benzodiazepine and the neurosteroid are nebulized. In some embodiments, the nebulized particles are about 3 μm or smaller. In some embodiments, the nebulized particles are about 2-3 μm. In some embodiments, one or both of the benzodiazepine and the neurosteroid are delivered to the distal alveoli. In some embodiments, one or both of the benzodiazepine and the neurosteroid are administered orally. In some embodiments, one or both of the benzodiazepine and the neurosteroid are contained within a soft gel capsule. In some embodiments, one or both of the benzodiazepine and the neurosteroid are administered parenterally. In some embodiments, one or both of the benzodiazepine and the neurosteroid are administered via a parenteral route selected from the group consisting of inhalational, intrapulmonary, intranasal, intramuscular, subcutaneous, transmucosal and intravenous. In some embodiments, one or both of the benzodiazepine and the neurosteroid are administered transmucosally. In varying embodiments, the method comprises co-administering a benzodiazepine and a neurosteroid formulated in a cyclodextrin, e.g., intramuscularly, intravenously and/or subcutaneously.

With respect to further embodiments of the methods, in some embodiments, the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the benzodiazepine is selected from the group consisting of midazolam, lorazepam, and diazepam. In some embodiments, the benzodiazepine is administered at a dose in the range of 0.3 µg/kg to 3.0 µg/kg. In varying embodiments, the benzodiazepine is administered at a dose that does not decrease blood pressure. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, allopregnanolone is co-administered with a benzodiazepine selected from the group consisting of midazolam, lorazepam, and diazepam. In some embodiments, the methods further comprise co-administration of an NMDA receptor antagonist. In some embodiments, the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine tenocyclidine, methoxydine, tiletamine, xenon, neramexane, eliprodil, etoxadrol, dexoxadrol, WMS 2539, NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13. In some embodiments, the NMDA receptor antagonist is selected from the group consisting of ketamine, dextromethorphan, phencyclidine, CPPene (3-[(R)-2-carboxypiperazin-4-yl]-prop-2-enyl-1-phosphonic acid), selfotel, amantadine, dextrorphan, memantine, tiletamine, neramexane, cliprodil, ramacemide, aptiganel, 1-Aminocyclopropanecarboxylic acid (ACPC). 7-Chlorokynurenate. DCKA (5,7-dichlorokynurenic acid), kynurenic acid, CP-101,606 (traxoprodil), AZD6765 (lanicemine) and GLYX-13. In some embodiments, the subject is experiencing aura. In some embodiments, the subject has been warned of an impending seizure. In some embodiments, the subject is experiencing a seizure. In some embodiments, the subject has status epilepticus, refractory status epilepticus or super-refractory status epilepticus. In some embodiments, the subject has myoclonic epilepsy. In some embodiments, the subject suffers from seizure clusters. In some embodiments, the seizure is a tonic seizure. In some embodiments, the seizure is a clonic seizure. In some embodiments, the subject has been exposed to or is at risk of being exposed to a nerve agent or a pesticide that can cause seizures. In some embodiments, the subject has been exposed to or is at risk of being exposed to tetramethylenedisulfotetramine (TETS).

In another aspect, further provided are kits comprising a benzodiazepine and a neurosteroid. In varying embodiments, one or both of the benzodiazepine and the neurosteroid are provided in unit dosage forms comprising a subtherapeutic dose. In some embodiments, the kits further comprise a NMDA receptor antagonist. In some embodiments, one or both of the benzodiazepine and the neurosteroid is formulated for inhalational, intranasal or intrapulmonary administration. In some embodiments, one or both of the benzodiazepine and the neurosteroid is formulated for oral or parenteral delivery. In some embodiments, one or both of the benzodiazepine and the neurosteroid are formulated for a parenteral route selected from the group consisting of inhalational, intrapulmonary, intranasal, intramuscular, subcutaneous, transmucosal and intravenous. In some embodiments, the benzodiazepine is an agonist of the benzodiazepine recognition site on $GABA_A$ receptors and stimulates endogenous neurosteroid synthesis. In some embodiments, the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the benzodiazepine is selected from the group consisting of midazolam, lorazepam and diazepam. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the neurosteroid is allopregnanolone. In some embodiments, the kit comprises allopregnanolone and a benzodiazepine selected from the group consisting of midazolam, lorazepam, and diazepam. In some embodiments, the neurosteroid is suspended or dissolved in a cyclodextrin (e.g., an α-cyclodextrin, a β-cyclodextrin or a γ-cyclodextrin). In varying embodiments, the neurosteroid is suspended or dissolved in a cyclodextrin selected from the group consisting of hydroxypropyl-β-cyclodextrin, endotoxin controlled β-cyclodextrin sulfobutyl ethers, or cyclodextrin sodium salts (e.g., CAPTISOL®). In some embodiments, the neurosteroid is suspended or dissolved in an edible oil. In some embodiments, the edible oil comprises one or more vegetable oils. In some embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof. In some embodiments, the edible oil is canola oil. In some embodiments, the edible oil comprises one or more nut oils. In some embodiments, the nut oil is selected from the group consisting of almond oil, cashew oil, hazelnut oil, macadamia oil, mongongo nut oil, pecan oil, pine nut oil, pistachio oil, walnut oil, and mixtures thereof. In some embodiments, the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid), CPPene (3-[(R)-2- carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine, tenocyclidine, methoxydine, tiletamine, xenon, neramexane, eliprodil, etoxadrol, dexoxadrol, WMS 2539, NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13. In some embodiments, the NMDA receptor antagonist is selected from the group consisting of ketamine, dextromethorphan, phencyclidine. CPPene (3-[(R)-2-carboxypiperazin-4-yl]-prop-2-enyl-1-phosphonic acid), selfotel, amantadine, dextrorphan, memantine, tiletamine, neramexane, eliprodil, remacemide, aptiganel, 1-Aminocyclopropanecarboxylic acid (ACPC), 7-Chlorokynurenate, DCKA (5,7-dichlorokynurenic acid), kynurenic acid, CP-101,606 (traxoprodil), AZD6765 (lanicemine) and GLYX-13. In some embodiments, the NMDA receptor antagonist is dizocilpine (MK-801).

In another aspect, the invention provides compositions comprising a benzodiazepine, a neurosteroid and an NMDA receptor antagonist. In some embodiments, the composition is formulated for inhalational or intrapulmonary administration. In some embodiments, the composition is formulated for oral or transmucosal delivery. In some embodiments, the benzodiazepine is an agonist of the benzodiazepine recognition site on $GABA_A$ receptors and stimulates endogenous neurosteroid synthesis. In some embodiments, the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the benzodiazepine is midazolam. In some embodiments, the benzodiazepine is diazepam. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the neurosteroid is allopregnanolone. In some embodiments, the neurosteroid is suspended or dissolved in a cyclodextrin (e.g., an α-cyclodextrin, a β-cyclodextrin or a γ-cyclodextrin). In varying embodiments, the neurosteroid is suspended or dissolved in a cyclodextrin selected from the group consisting of hydroxypropyl-β-cyclodextrin, endotoxin controlled β-cyclodextrin sulfobutyl ethers, or cyclodextrin sodium salts (e.g., CAPTISOL®). In some embodiments, the neurosteroid is suspended or dissolved in an edible oil. In some embodiments, the edible oil comprises one or more a vegetable oils. In some embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof. In some embodiments, the edible oil is canola oil. In some embodiments, the edible oil comprises one or more nut oils. In some embodiments, the nut oil is selected from the group consisting of almond oil, cashew oil, hazelnut oil, macadamia oil, mongongo nut oil, pecan oil, pine nut oil, pistachio oil, walnut oil, and mixtures thereof in some embodiments, the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine tenocyclidine, methoxydine, tiletamine, xenon, neramexane, cliprodil, etoxadrol, dexoxadrol, WMS 2539, NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil). AZD6765 (lanicemine) and GLYX-13. In some embodiments, the NMDA receptor antagonist is selected from the group consisting of ketamine, dextromethorphan, phencyclidine, CPPene (3-[(R)-2-carboxypiperazin-4-yl]-prop-2-enyl-1-phosphonic acid), selfotel, amantadine, dextrorphan, memantine, tiletamine, neramexane, eliprodil, remacemide, aptiganel, 1-Aminocyclopropanecarboxylic acid (ACPC), 7-Chlorokynurenate, DCKA (5,7-dichlorokynurenic acid), kynurenic acid, CP-101,606 (traxoprodil), AZD6765 (lanicemine) and GLYX-13.

In another aspect, the invention provides methods of preventing or terminating a seizure in a subject in need thereof, comprising administration to the subject of an effective amount of a composition as described above and herein. In another aspect, the invention provides methods of accelerating the termination or abortion of an impending seizure in a subject in need thereof, comprising administration to the subject of an effective amount of a composition as described above and herein. In a further aspect, the invention provides methods of preventing or terminating a seizure in a subject in need thereof, comprising administration to the subject of an effective amount of a benzodiazepine, a neurosteroid and an NMDA receptor antagonist. In a further aspect, the invention provides methods of accelerating the termination or abortion of an impending seizure in a subject in need thereof, comprising administration to the subject of an effective amount of a benzodiazepine, a neurosteroid and an NMDA receptor antagonist. In some embodiments, the benzodiazepine, neurosteroid and NMDA receptor antagonist are co-administered together and/or by the same route of administration. In some embodiments, the benzodiazepine, neurosteroid and NMDA receptor antagonist are co-administered separately and/or by different routes of administration. In some embodiments, the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid). CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine.tenocyclidine, methoxydine, tiletamine, xenon, neramexane, eliprodil, etoxadrol, dexoxadrol, WMS 2539, NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13. In some embodiments, the NMDA receptor antagonist is selected from the group consisting of ketamine, dextromethorphan, phencyclidine, CPPene (3-[(R)-2-carboxypiperazin-4-yl]-prop-2-enyl-1-phosphonic acid), selfotel, amantadine, dextrorphan, memantine, tiletamine, neramexane, eliprodil, remacemide, aptiganel, 1-Aminocyclopropanecarboxylic acid (ACPC), 7-Chlorokynurenate, DCKA (5,7-dichlorokynurenic acid), kynurenic acid, CP-101,606 (traxoprodil), AZD6765 (lanicemine) and GLYX-13. In one embodiment, the subject is experiencing aura. In one embodiment, the subject has been warned of an impending seizure. In one embodiment, the subject is experiencing a seizure. In one embodiment, the subject has status epilepticus, refractory status epilepticus or super-refractory status epilepticus. In one embodiment, the subject has myoclonic epilepsy. In one embodiment, the subject suffers from seizure clusters. In one embodiment, the seizure is a tonic seizure. In one embodiment, the seizure is a clonic seizure. In one embodiment, the benzodiazepine is self-administered by the subject. In one embodiment, the composition is administered via inhalational or intrapulmonary administration. In one embodiment, the composition is not heated prior to administration. In one embodiment, the benzodiazepine is nebulized. In one embodiment, the nebulized particles are about 3 µm or smaller. In one embodiment, the nebulized particles are about 2.3 µm. In one embodiment, the benzodiazepine is delivered to the distal alveoli. In one embodiment, the benzodiazepine is administered at a dose in the range of 0.3 µg/kg to 3.0 µg/kg. In varying embodiments, the benzodiazepine is administered at a dose that does not decrease blood pressure. In one embodiment, the composition is administered orally. In one embodiment, the composition is contained within a soft gel capsule. In one embodiment, the composition is administered transmucosally. In various embodiments, the subject may be at risk of exposure to or may have been exposed to tetramethylenedisulfotetramine (TETS).

Definitions

As used herein, "administering" refers to local and systemic administration, e.g., including enteral, parenteral, pulmonary, and topical/transdermal administration. Routes of administration for the agents (e.g., one or more of a benzodiazepine, a neurosteroid and/or an NMDA receptor antagonist) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, iontophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administration" refers to the presence of both active agents in the blood at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The term "effective amount" or "pharmaceutically effective amount" refer to the amount and/or dosage, and/or dosage regime of one or more compounds necessary to bring about the desired result e.g., an amount sufficient prevent, abort or terminate a seizure.

"Sub-therapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to abort or prevent a seizure), or that quantitatively is less than the established therapeutic dose for that particular pharmacological agent (e g, as published in a reference consulted by a person of skill, for example, doses for a pharmacological agent published in the Physicians' Desk Reference, 67th Ed, 2013, Thomson Healthcare or Brunton, et al., Goodman & Gilman's The Pharmacological Basis of Therapeutics, 12th edition, 2010, McGraw-Hill Professional). A "sub-therapeutic dose" can be defined in relative terms (i.e., as a percentage amount (less than 100%) of the amount of pharmacologically active agent conventionally administered). For example, a sub-therapeutic dose amount can be about 1% to about 75% of the amount of pharmacologically active agent conventionally administered. In some embodiments, a sub-therapeutic dose can be less than about 75%, 50%, 30%, 25%, 20%, 10% or less, than the amount of pharmacologically active agent conventionally administered A sub-therapeutic dose amount can be in the range of about 1% to about 75% of the amount of pharmacologically active agent known to elicit the intended pharmacological effect. In some embodiments, a sub-therapeutic dose can be less than about 75%, 50%, 30%, 25%, 20%, 10% or less, than the amount of pharmacologically active agent known to elicit the intended pharmacological effect.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "reduce," "inhibit," "relieve," "alleviate" refer to the detectable decrease in the frequency, severity and/or duration of seizures. A reduction in the frequency, severity and/or duration of seizures can be measured by self-assessment (e.g., by reporting of the patient) or by a trained clinical observer. Determination of a reduction of the frequency, severity and/or duration of seizures can be made by comparing patient status before and after treatment.

As used herein, the phrase "consisting essentially of" refers to the genera or species of active pharmaceutical agents (e.g., neurosteroid in combination with benzodiazepine, optionally in further combination with an NMDA blocker) and excipient (e.g., a cyclodextrin, an edible oil) included in a method or composition. In various embodiments, other unmentioned or unrecited active ingredients and inactive are expressly excluded. In various embodiments, additives (e.g., surfactants, acids (organic or fatty), alcohols, esters, co-solvents, solubilizers, lipids, polymers, glycols) are expressly excluded.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

The term "edible oil" refers to an oil that is digestible by a mammal. Preferred oils are edible or digestible without inducing undesirable side effects.

The term "neuroactive steroid" or "neurosteroid" refers to steroid compounds that rapidly alter neuronal excitability through interaction with neurotransmitter-gated ion channels. Neurosteroids act as allosteric modulators of neurotransmitter receptors, such as $GABA_A$, NMDA, and sigma receptors. Neurosteroids find use as sedatives for the purpose of general anaesthesia for carrying out surgical procedures, and in the treatment of epilepsy and traumatic brain injury. Illustrative neurosteroids include, e.g., allopregnanolone, Ganaxolone, alphaxolone, alphadolone, hydroxydione, minaxolone, and Althesin (a mixture of alphaxolone and alphadolone).

(A) Representative traces illustrating effects of pre-exposure to increasing concentrations of allopregnanolone (0.03-1 µM) on TETS-induced Ca2+ dysregulation. (B) Effect of allopregnanolone (AlloP) on TETS-induced increase in integrated Ca2+ levels in Phase I. (C,D) Effect of allopregnanolone on the TETS-induced synchronous Ca2+ transient oscillation frequency decrease (C) and amplitude increase (D) in Phase II. **, p<0.01, TETS vs. vehicle control, #, p<0.05, ##, p<0.01, allopregnanolone+TETS vs TETS, n=6 pooled from two experiments.

FIGS. 9A-D illustrate low concentrations of allopregnanolone and diazepam in combination act synergistically to mitigate TETS-induced neuronal Ca2+ signaling dysregulation. (A) Representative traces illustrating effect of pre-exposure to allopregnanolone (0.1 µM), diazepam (0.1 µM) or a combination of allopregnanolone (0.1 µM) and diazepam (0.1 µM) on TETS-induced Ca2+ dysregulation. (C,D) Effects of allopregnanolone or diazepam alone or the combination on TETS-induced synchronous Ca2+ transient oscillation frequency decrease (C) and amplitude increase (D) in phase II. **, p<0.01, TETS vs. vehicle control, ##, p<0.01, allopregnanolone/diazepam+TETS vs TETS, n=8 pooled from two experiments.

Figure 10A:
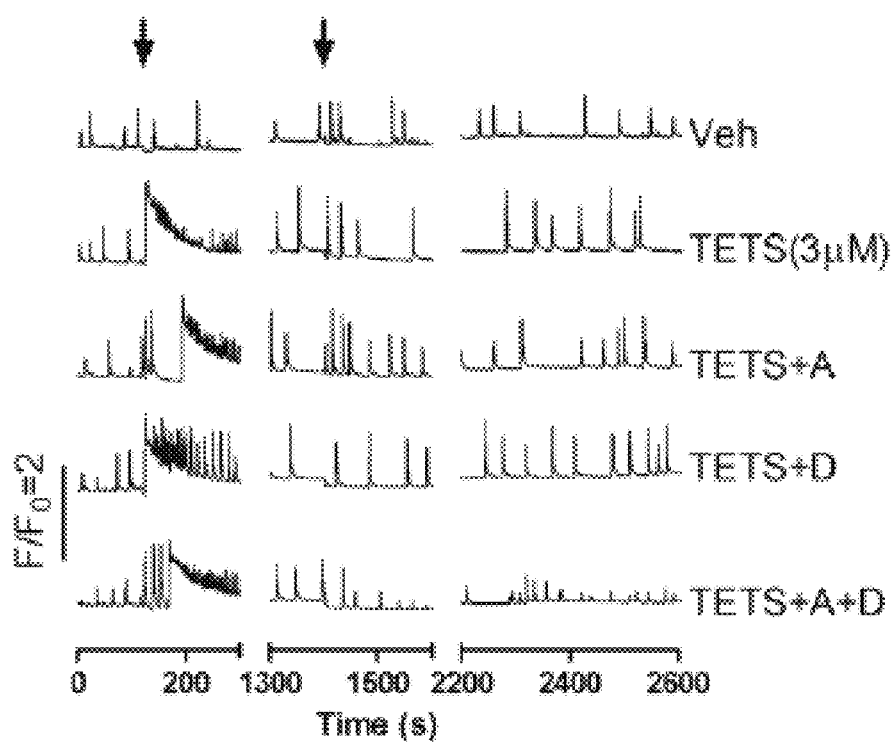
Figure 10B:
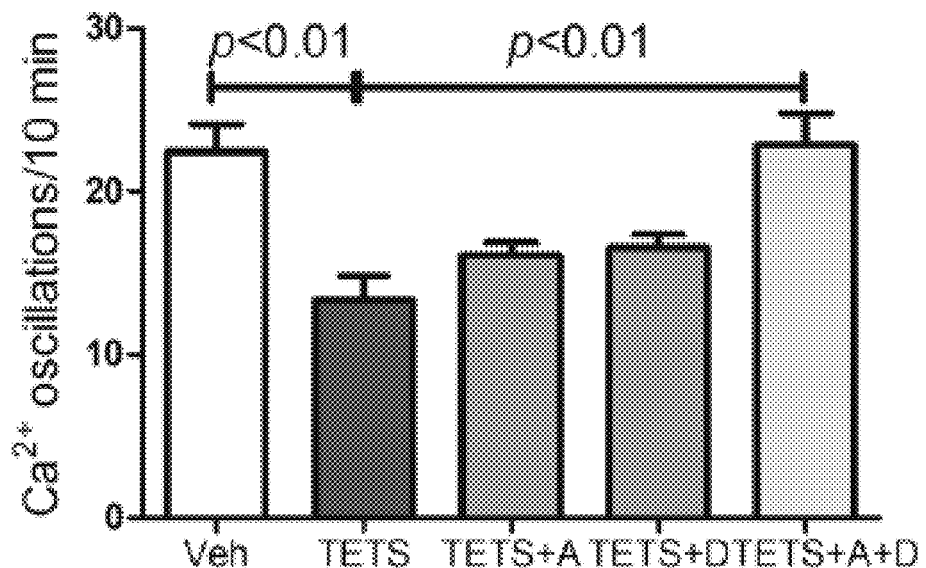
Figure 10C:
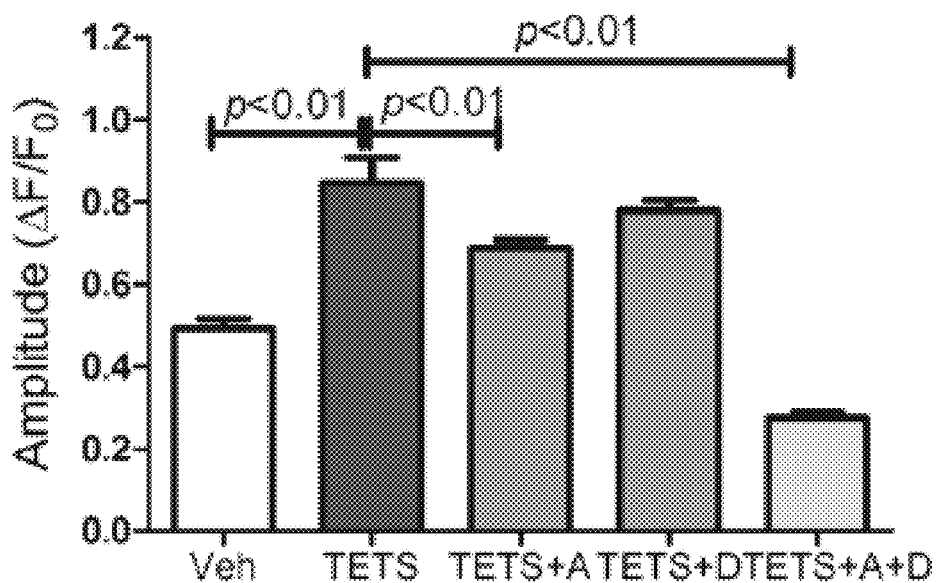

FIGS. 10A-C illustrate that exposure of mouse hippocampal neurons following TETS challenge with diazepam (0.1 µM) and allopregnanolone (0.1 µM) in combination effectively mitigates TETS dysregulated Ca2+ dynamics. (A) Representative traces illustrating effects of post-TETS treatment with diazepam or allopregnanolone or the combination on TETS-induced $Ca^{2+}$ dysregulation. Amelioration of TETS-induced alterations in the Phase II response (see, Cao et al, *Toxicological Sciences* (2012) 130:362-372) by diazepam and allopregnanolone, either singly or in combination, on the frequency of synchronous $Ca^{2+}$ oscillation (B) and increases in $Ca^{2+}$ transient amplitude (C). The first arrowhead indicates the addition of TETS or vehicle. The second arrowhead indicates the addition of vehicle or diazepam or allopregnanolone or the combination. Each data point represents Mean±SEM, n=6 wells.

Figure 11:
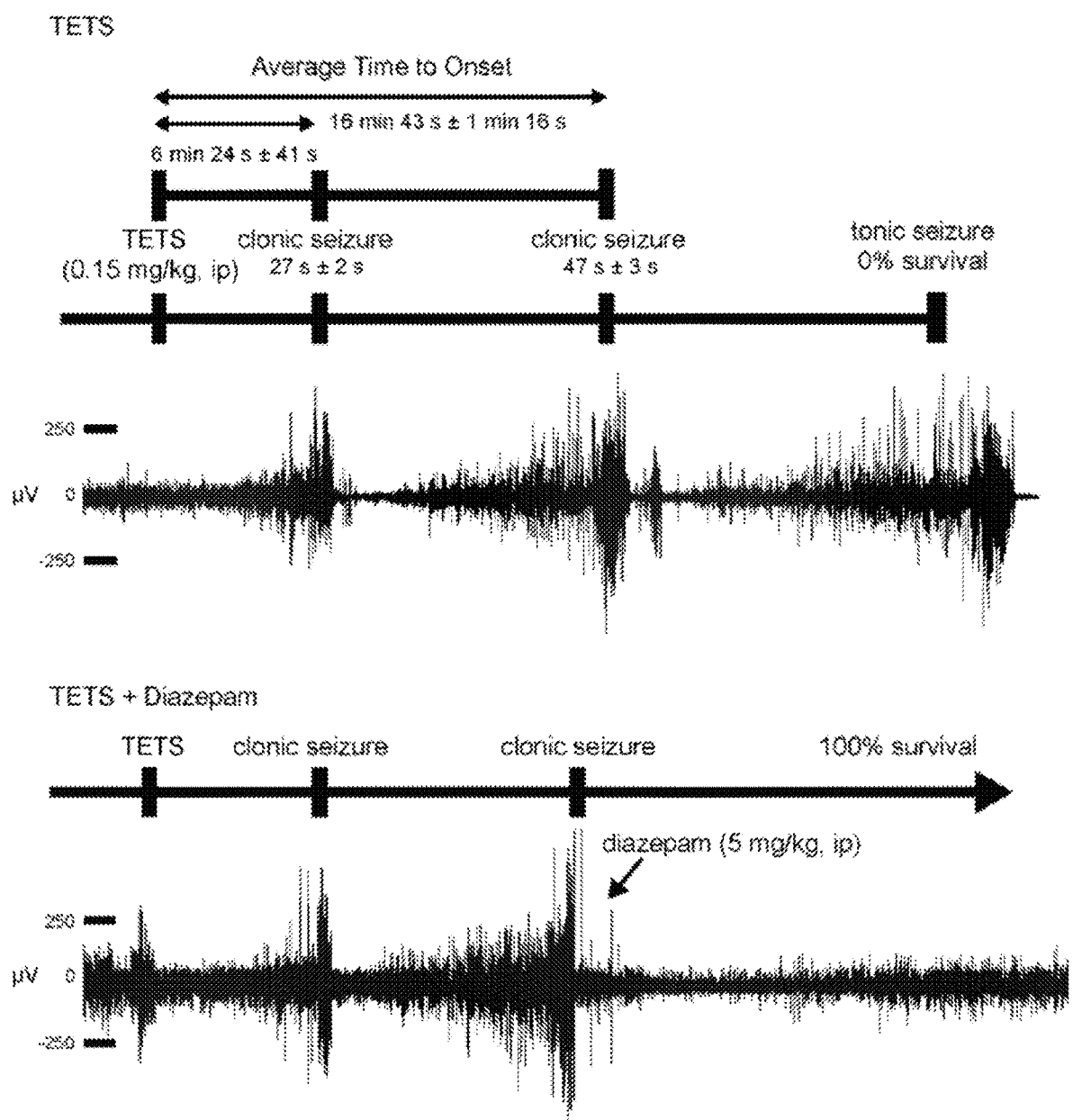

FIG. 11 illustrates that high dose diazepam rescues animals from TETS-induced tonic seizures and death. Representative EEG recordings from mice administered TETS (0.15 mg/kg, i.p.) with and without pretreatment with diazepam (dose/route). Time to seizure onset and seizure duration are expressed as the mean±S.E.M. (n=x per treatment group). Administration of diazepam immediately following the second clonic seizure prevented a fatal tonic seizure. EEG recording in TETS-exposed animals rescued by diazepam indicated no additional seizure for up to 1 h post-TETS exposure.

Figure 12:
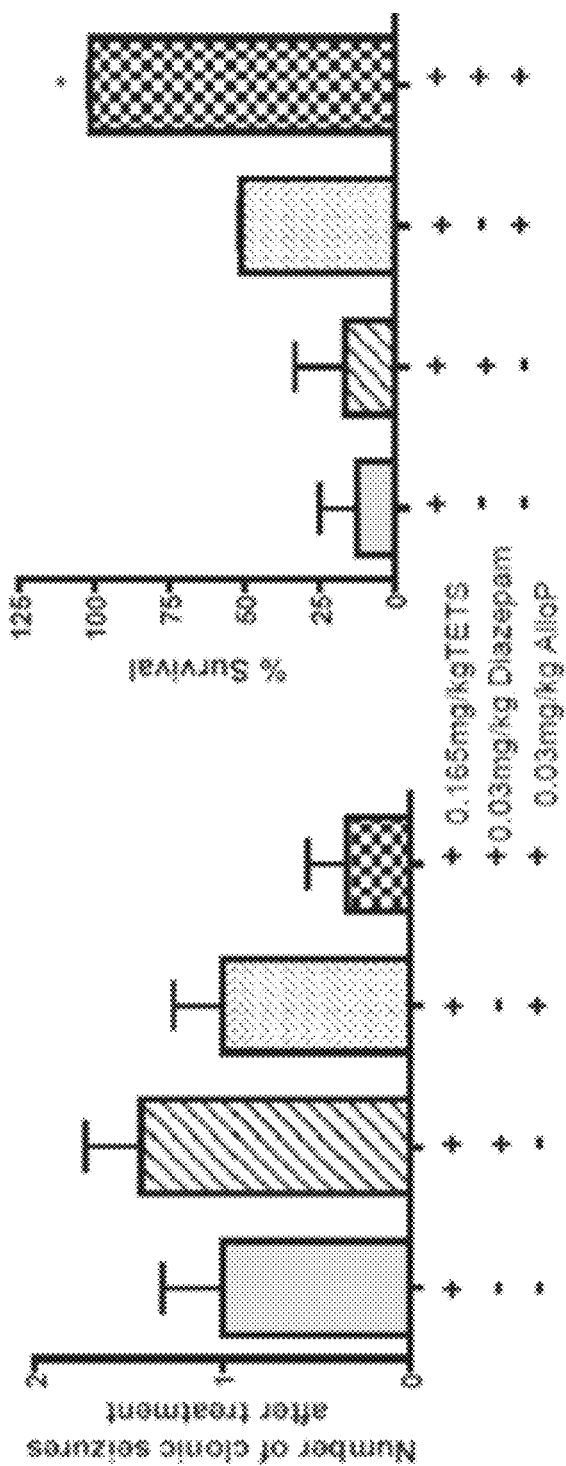

FIG. 12. Adult male NIH Swiss mice were injected with TETS (i.p.). Two minutes following the second clonic seizure, mice were injected i.p. with diazepam (in saline) or allopregnanolone (AlloP, in β-cyclodextrin) singly or in combination. Seizure time to onset, number and duration were monitored for 1 h post-TETS exposure. % Survival is at 24 h post TETS injection. Data presented as the mean±SEM (n=6-8 per group). **p<0.05 as determined by one way ANOVA with Tukey's post hoc test.

Figure 13:
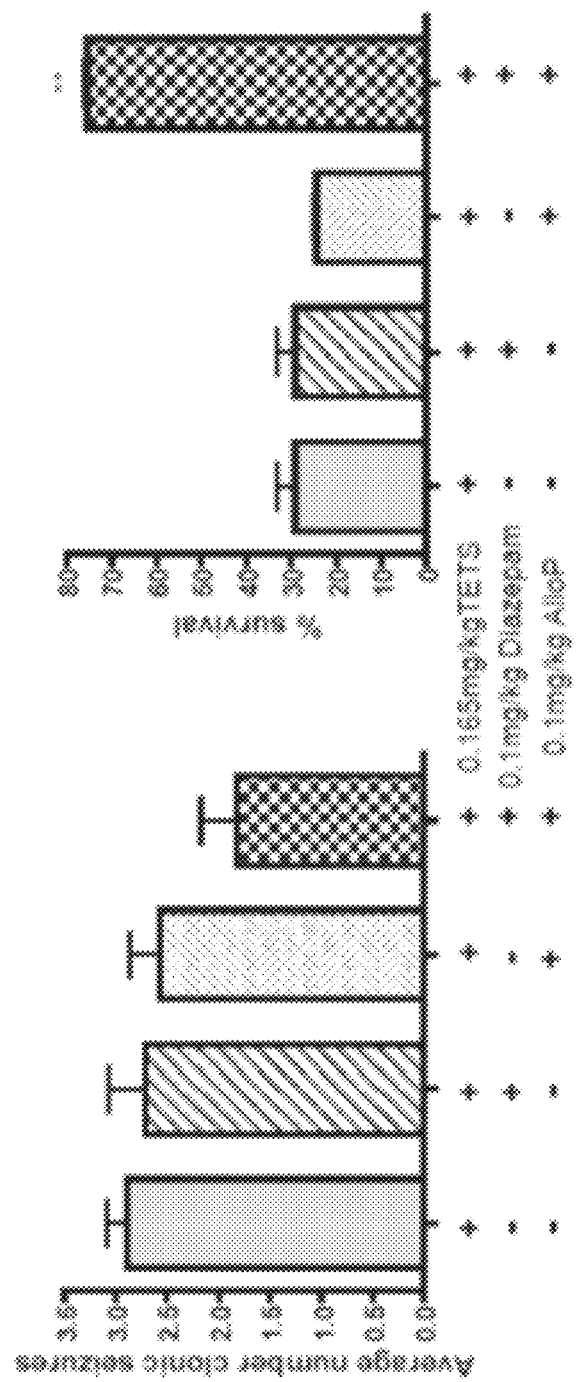

FIG. 13. Adult male NIH Swiss mice were injected i.p. with diazepam (in saline) or allopregnanolone (AlloP, in β-cyclodextrin) singly or in combination 10 minutes prior to i.p. injection of TETS. Seizure time to onset, duration and number were monitored for 1 h post TETS injection. % Survival is at 24 h post TETS injection. Data presented as the mean±SEM (n=8 per group). **p<0.01 as determined by one way ANOVA with Tukey's post hoc test.

Figure 14:
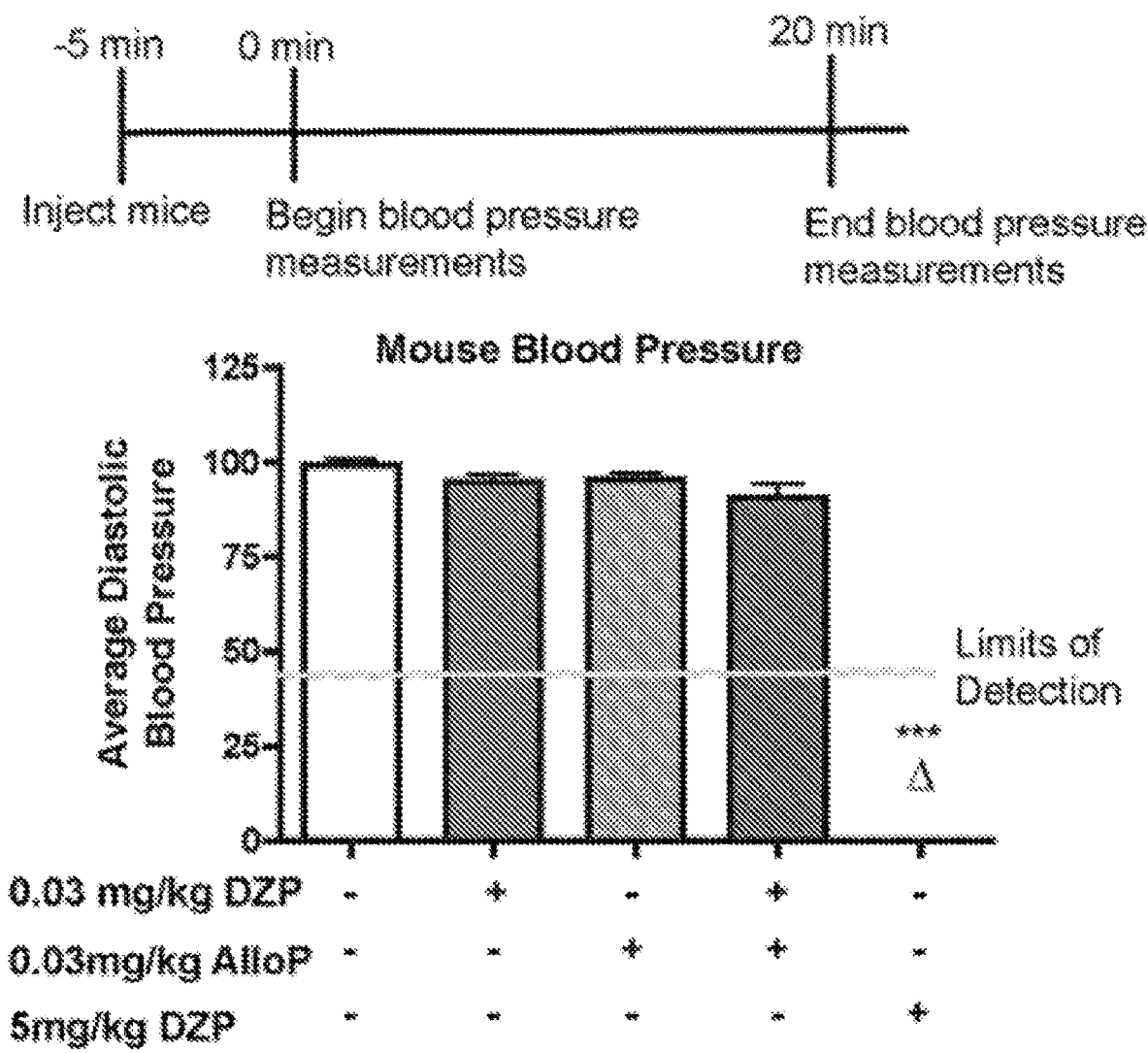

FIG. 14 illustrates the effect of benzodiazepine and neurosteroid treatments on blood pressure. Adult male NIH Swiss mice were i.p. injected with diazepam (DZP) or allopregnanolone (AlloP) alone or in combination. Blood pressure (BP) was measured using a tail cuff CODA non-invasive blood measuring system from Kent Scientific. This system utilizes volume pressure recording technology to detect changes that correspond to systolic and diastolic BP. Diastolic BP is measured and systolic BP calculated. BP is measured for 6 days prior to testing to obtain baseline BP and allow animals to acclimate to the chamber. Measurements consisted of 20 cycles of 30 sec each with 10 sec delay between each measurement. Data presented as the mean±SEM (n=6 per group).

DETAILED DESCRIPTION

1. Introduction

Tetramethylenedisulfotetramine (TETS) is a potent convulsant that is considered a chemical threat agent. We characterized TETS as an activator of spontaneous Ca2· oscillations and electrical burst discharges in mouse hippocampal neuronal cultures at 13-17 days in vitro using FLIPR® Fluo-4 fluorescence measurements and extracellular multielectrode array (MEA) recording Acute exposure to TETS (≥2 µM) reversibly altered the pattern of spontaneous neuronal discharges, producing clustered burst firing and an overall increase in discharge frequency TETS also dramatically affected Ca2+ dynamics causing an immediate but transient elevation of neuronal intracellular Ca2− followed by decreased frequency of Ca2| oscillations having greater peak amplitudes. The effect on Ca2| dynamics was similar to that elicited by picrotoxin and bicuculline, supporting the view that TETS acts by inhibiting $GABA_A$ receptor function. The effect of TETS on Ca2| dynamics requires activation of NMDA receptors, since the changes induced by TETS were prevented by MK-801 block of NMDA receptors, but not nifedipine block of L-type Ca2− channels. Pre-treatment with the $GABA_A$ receptor positive modulators diazepam and allopregnanolone partially mitigated TETS-induced changes in Ca2− dynamics. Moreover, low, minimally effective concentrations of diazepam (0.1 µM) and allopregnanolone (0.1 µM), when administered together, were highly effective in suppressing TETS-induced alterations in Ca2· dynamics, suggesting that the combination of positive modulators synaptic and extrasynaptic $GABA_A$ receptors have therapeutic potential. These rapid throughput in vitro assays may assist in the identification of single agents or combinations that have utility in the treatment of TETS intoxication.

2. Conditions Amenable to Treatment

Co-administration of a benzodiazepine and a neurosteroid. In varying embodiments, one or both of the benzodiazepine and the neurosteroid are administered in a sub-therapeutic dose or amount finds use in the rapid amelioration and/or termination of seizures. In various embodiments, the seizures may be due to an epileptic condition. Optionally, an NMDA receptor antagonist is also co-administered.

The term "epilepsy" refers to a chronic neurological disorder characterized by recurrent unprovoked seizures. These seizures are transient signs and/or symptoms of abnormal, excessive or synchronous neuronal activity in the brain. There are over 40 different types of epilepsy, including without limitation childhood absence epilepsy, juvenile absence epilepsy, benign Rolandic epilepsy, clonic seizures, complex partial seizures, frontal lobe epilepsy, febrile seizures, infantile spasms, juvenile myoclonic epilepsy, Lennox-Gastaut syndrome, Landau-Kleffner Syndrome, myoclonic seizures, mitochondrial disorders associated with seizures, Lafora Disease, progressive myoclonic epilepsies, reflex epilepsy, and Rasmussen's syndrome. There are also numerous types of seizures including simple partial seizures, complex partial seizures, generalized seizures, secondarily generalized seizures, temporal lobe seizures, tonic-clonic seizures, tonic seizures, psychomotor seizures, limbic seizures, status epilepticus, refractory status epilepticus or super-refractory status epilepticus, abdominal seizures, akinetic seizures, autonomic seizures, massive bilateral myoclonus, drop seizures, focal seizures, gelastic seizures, Jacksonian march, motor seizures, multifocal seizures, neonatal seizures, nocturnal seizures, photosensitive seizure, sensory seizures, sylvan seizures, withdrawal seizures and visual reflex seizures.

The most widespread classification of the epilepsies divides epilepsy syndromes by location or distribution of seizures (as revealed by the appearance of the seizures and by EEG) and by cause. Syndromes are divided into localization-related epilepsies, generalized epilepsies, or epilepsies of unknown localization. Localization-related epilepsies, sometimes termed partial or focal epilepsies, arise from an epileptic focus, a small portion of the brain that serves as the irritant driving the epileptic response. Generalized epilepsies, in contrast, arise from many independent foci (multifocal epilepsies) or from epileptic circuits that involve the whole brain. Epilepsies of unknown localization remain unclear whether they arise from a portion of the brain or from more widespread circuits.

Epilepsy syndromes are further divided by presumptive cause idiopathic, symptomatic, and cryptogenic. Idiopathic epilepsies are generally thought to arise from genetic abnormalities that lead to alterations in brain excitability. Symptomatic epilepsies arise from the effects of an epileptic lesion, whether that lesion is focal, such as a tumor, or a defect in metabolism causing widespread injury to the brain. Cryptogenic epilepsies involve a presumptive lesion that is otherwise difficult or impossible to uncover during evaluation. Forms of epilepsy are well characterized and reviewed, e.g. in Epilepsy: A Comprehensive Textbook (3-volume set), Engel, et al., editors, 2nd Edition, 2007, Lippincott, Williams and Wilkins; and The Treatment of Epilepsy: Principles and Practice, Wyllie, et al., editors, 4th Edition, 2005, Lippincott, Williams and Wilkins; and Browne and Holmes, Handbook of Epilepsy, 4th Edition, 2008, Lippincott, Williams and Wilkins.

3. Subjects Amenable to Treatment

In various embodiments, the patient may be experiencing an electrographic or behavioral seizure or may be experiencing a seizure aura, which itself is a localized seizure that may spread and become a full blown behavioral seizure. For example, the subject may be experiencing aura that alerts of the impending onset of a seizure or seizure cluster.

Alternatively, the subject may be using a seizure prediction device that alerts of the impending onset of a seizure or seizure cluster. Implantable seizure prediction devices are known in the art and described, e.g., in D'Alessandro, et al., IEEE TRANSACTIONS ON BIOMEDICAL ENGINEERING, VOL. 50. NO. 5. MAY 2003, and U.S. Patent Publication Nos. 2010/0198098, 2010/0168603, 2009/0062682, and 2008/0243022.

The subject may have a personal or familial history of any of the epileptic conditions described herein. The subject may have been diagnosed as having any of the epileptic conditions described herein. In some embodiments, the subject has or is at risk of suffering status epilepticus, refractory status epilepticus or super-refractory status epilepticus. In some embodiments, the subject has or is at risk of suffering a myoclonic seizure or myoclonic epilepsy, e.g., juvenile myoclonic epilepsy. The PTZ seizure model demonstrated herein is predictive of utility and/or activity in counteracting myoclonic seizures or myoclonic epilepsy in humans.

In various embodiments, the subject may be at risk of exposure to or may have been exposed to tetramethylenedisulfotetramine (TETS).

In various embodiments, the subject may be at risk of exposure to or may have been exposed to a nerve agent or a pesticide that can cause seizures. Illustrative nerve agents that can cause seizures include, e.g., organophosphorus nerve agents, e.g., tabun, sarin, soman, GF, VR and/or VX. Illustrative pesticides that can cause seizures include, e.g., organophosphate pesticides (e.g., Acephate (Orthene), Azinphos-methyl (Gusathion, Guthion), Bensulide (Betasan, Lescosan), Bomyl (Swat), Bromophos (Nexion), Bromophos-ethyl (Nexagan), Cadusafos (Apache, Ebufos, Rugby), Carbophenothion (Trithion), Chlorethoxyfos (Fortress), Chlorfenvinphos (Apachlor, Birlane), Chlormephos (Dotan), Chlorphoxim (Baython-C), Chlorpyrifos (Brodan, Dursban, Lorsban), Chlorthiophos (Celathion), Coumaphos (Asuntol, Co-Ral), Crotoxyphos (Ciodrin, Cypona), Crufomate (Ruelene), Cyanofenphos (Surecide), Cyanophos (Cyanox), Cythioate (Cyflee, Proban), DEF (De-Green), E-Z-Off D), Demeton (Systox), Demeton-S-methyl (Duratox, Metasystoxl), Dialifor (Torak), Diazinon, Dichlorofenthion, (VC-13 Nemacide), Dichlorvos (DDVP, Vapona), Dicrotophos (Bidrin), Dimefos (Hanane, Pestox XIV), Dimethoate (Cygon, DeFend), Dioxathion (Delnav), Disulfoton (Disyston), Ditalimfos, Edifenphos, Endothion, EPBP (S-seven), EPN, Ethion (Ethanox), Ethoprop (Mocap), Ethyl parathion (E605, Parathion, thiophos), Etrimfos (Ekamet), Famphur (Bash, Bo-Ana, Famfos), Fenamiphos (Nemacur), Fenitrothion (Accothion, Agrothion, Sumithion), Fenophosphon (Agritox, trichloronate), Fensulfothion (Dasanit), Fenthion (Baytex, Entex, Tiguvon), Fonofos (Dyfonate, N-2790), Formothion (Anthio), Fosthietan (Nem-A-Tak), Heptenophos (Hostaquick), Hiometon (Ekatin), Hosalone (Zolone), IBP (Kitazin), Iodofenphos (Nuvanol-N), Isazofos (Brace, Miral, Triumph), Isofenphos (Amaze, Oftanol), Isoxathion (E-48, Karphos), Leptophos (Phosvel), Malathion (Cythion), Mephosfolan (Cytrolane), Merphos (Easy Off-D, Folex), Methamidophos (Monitor), Methidathion (Supracide, Ultracide), Methyl parathion (E601. Penncap-M). Methyl trithion, Mevinphos (Duraphos, Phosdrin), Mipafox (Isopestox, Pestox XV), Monocrotophos (Azodrin), Naled (Dibrome), Oxydemeton-methyl (Metasystox-R), Oxydeprofos (Metasystox-S), Phencapton (G 28029), Phenthoate (Dimephenthoate, Phenthoate), Phorate (Rampart, Thimet), Phosalone (Azofene, Zolone), Phosfolan (Cylan, Cyolane), Phosmet (Imidan, Prolate), Phosphamidon (Dimecron), Phostebupirim (Aztec), Phoxim (Baython), Pirimiphos-ethyl (Primicid), Pirimiphos-methyl (Actellic), Profenofos (Curacron), Propetamphos (Safrotin), Propyl thiopyrophosphate (Aspon), Prothoate (Fac), Pyrazophos (Afugan, Curamil), Pyridaphenthion (Ofunack), Quinalphos (Bayrusil), Ronnel (Fenchlorphos, Korlan), Schradan (OMPA), Sulfotep (Bladafum, Dithione, Thiotepp), Sulprofos (Bolstar, Helothion), Temephos (Abate, Abathion), Terbufos (Contraven, Counter), Tetrachlorvinphos (Gardona, Rabon), Tetraethyl pyrophosphate (TEPP), Triazophos (Hostathion), and Trichlorfon (Dipterex, Dylox, Neguvon, Proxol).

4. Therapeutic Agents

Generally, the compositions and methods comprise co-administering a benzodiazepine and a neurosteroid. In varying embodiments, one or both of the benzodiazepine and the neurosteroid are co-administered at a sub-therapeutic dose or amount. Optionally, an NMDA receptor antagonist is co-administered. The agents can be co-administered concurrently or sequentially. The agents can be co-administered via the same or different routes of administration. In various embodiments, the agents are co-administered in a single composition.

a. Benzodiazepines

Any benzodiazepine known in the art finds use in the present compositions and methods. Illustrative benzodiazepine that find use include without limitation bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the benzodiazepine is midazolam. In some embodiments, the benzodiazepine is diazepam.

b. Neurosteroids

The terms "neuroactive steroid" or "neurosteroids" interchangeably refer to steroids that rapidly alter neuronal excitability through interaction with neurotransmitter-gated ion channels, specifically $GABA_A$ receptors Neuroactive steroids have a wide range of applications from sedation to treatment of epilepsy and traumatic brain injury. Neuroactive steroids act as direct agonists and allosteric positive modulators of $GABA_A$ receptors. Several synthetic neuroactive steroids have been used as sedatives for the purpose of general anaesthesia for carrying out surgical procedures. Exemplary sedating neuroactive steroids include without limitation alphaxolone, alphadolone, hydroxydione and minaxolone. The neuroactive steroid ganaxolone finds use for the treatment of epilepsy. In various embodiments, the benzodiazepine or non-benzodiazepine benzodiazepine receptor agonist is co-administered with an endogenously occurring neurosteroid or other neuroactive steroid. Illustrative endogenous neuroactive steroids, e.g., allopregnanolone and tetrahydrodeoxycorticosterone find use. In some embodiments, the neurosteroid is selected from the group consisting of allopregnanolone, allotetrahydrodeoxycorticosterone, ganaxolone, alphaxolone, alphadolone, hydroxydione, minaxolone, and Althesin.

In various embodiments the neurosteroid is allopregnanolone (ALP) Allopregnanolone, also known as 3α-hydroxy-5α-pregnan-20-one or 3α,5α-tetrahydroprogesterone, IUPAC name 1-(3-Hydroxy-10,13-dimethyl-2,3,4,5,6,7,8,9,11,12,14,15,16,17-tetradecahydro-1H-cyclopenta[a]phenanthren-17-yl)ethanone, and referenced as CAS number 516-54-1, is a prototypic neurosteroid present in the blood and also the brain. It is a metabolite of progesterone and modulator of $GABA_A$ receptors. While allopregnanolone, like other $GABA_A$ receptor active neurosteroids such as allotetrahydrodeoxycorticosterone (3α,21-dihydroxy-5α-pregnan-20-one; THDOC), positively modulates all $GABA_A$ receptor isoforms, those isoforms containing δ-subunits exhibit greater magnitude potentiation Allopregnanolone has pharmacological properties similar to other positive modulators of $GABA_A$ receptors, including anxiolytic and anticonvulsant activity. Allopregnanolone is neuroprotective in many animal models of neurodegenerative conditions, including, e.g., Alzheimer's disease (Wang et al, *Proc Natl Acad Sci USA.* 2010 Apr. 6; 107(14):6498-503), cerebral edema (Limmroth et al., *Br J Pharmacol.* 1996 January; 117(1):99-104) and traumatic brain injury (He et al., *Restor Neurol Neurosci.* 2004; 22(1):19-31; and He, et al., *Exp Nerol.* 2004 October; 189(2):404-12), Mood disorders (Robichaud and Debonnel, *Int J Neuropsychopharmacol.* 2006 April; 9(2): 191-200), Niemann-Pick type C disease (Griffin et al., *Nat Med.* 2004 July, 10(7) 704-11) and acts as an anticonvulsant against chemically induced seizures, including the pentylentetrazol (PTZ) model (Kokate et al., *J Pharmacol Exp Ther.* 1994 September; 270(3) 1223-9) The chemical structure of allopregnanolone is depicted below in Formula I:

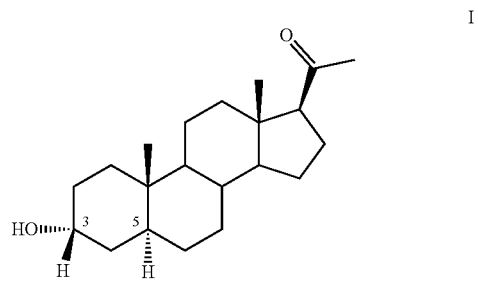 [SMILES: CC(=O)[C@H]1CCC2C3CC[C@H]4C[C@H](O)CC[C@]4(C)C3CC[C@@]21C]

In various embodiments, the compositions comprise a sulfate, salt, hemisuccinate, nitrosylated, derivative or congener of allopregnanolone.

Delivery of other neurosteroids also can be enhanced by formulation in a cyclodextrin and/or in an edible oil. Other neurosteroids that can be formulated in a cyclodextrin and/or in an edible oil, include without limitation allotetrahydrodeoxycorticosterone (3α,21-dihydroxy-5α-pregnan-20-one; THDOC), 3 α,21-dihydroxy-5b-pregnan-20-one, pregnanolone (3α-hydroxy-5β-pregnan-20-one), Ganaxolone (INN, also known as CCD-1042; IUPAC name (3α,5α)-3-hydroxy-5-methylpregnan-20-one; 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl]ethanone), alphaxolone, alphadolone, hydroxydione, minaxolone, and Althesin (a mixture of alphaxolone, alphadolone, tetrahydrodeoxycorticosterone, pregnenolone, dehydroepiandrosterone (DHEA), 7-substituted benz[c]indene-3-carbonitriles (see, e.g., Hu, et al., *J Med Chem.* (1993) 36(24):3956-67); 7-(2-hydroxyethyl)benz[e]indene analogues (see, e.g., Han, et al., *J Med Chem.* (1995) 38(22):4548-56); 3 alpha-hydroxy-5 alpha-pregnan-20-one and 3 alpha-hydroxy-5 beta-pregnan-20-one analogues (see. e.g., Han, et al., *J Med Chem.* (1996) 39(21): 4218-32); enantiomers of dehydroepiandrosterone sulfate, pregnenolone sulfate, and (3alpha,5beta)-3-hydroxypregnan-20-one sulfate (see, e.g., Nilsson, et al., *J Med Chem.* (1998) 41(14):2604-13): 13,24-cyclo-18,21-dinorcholane analogues (see, e.g., Jiang, et al, *J Med Chem.* (2003) 46(25):5334-48): N-acylated 17a-aza-D-homosteroid analogues (see, e.g., Covey, et al, *J Med Chem.* (2000) 43(17): 3201-4); 5 beta-methyl-3-ketosteroid analogues (see, e.g., Zeng, et al., *J Org Chem.* (2000) 65(7):2264-6); 18-norandrostan-17-one analogues (see, e.g., Jiang, et al., *J Org Chem.* (2000) 65(11):3555-7); (3alpha,5alpha)- and (3alpha, 5beta)-3-hydroxypregnan-20-one analogs (see. e.g., Zeng, et al., *J Med Chem.* (2005) 48(8):3051-9); benz[f]indenes (see, e.g., Scaglione, et al., *J Med Chem.* (2006) 49(15):4595-605); enantiomers of androgens (see, e.g., Katona, et al., *Eur J Med Chem.* (2008) 43(1): 107-13), cyclopenta[b] phenanthrenes and cyclopenta[b]anthracenes (see, e.g., Scaglione, et al., *J Med Chem.* (2008) 51(5) 1309-18), 2beta-hydroxygonane derivatives (see, e.g., Wang, et al., *Tetrahedron* (2007) 63(33):7977-7984), Δ16-alphaxalone and corresponding 17-carbonitrile analogues (see, e.g., Bandyopadhyaya, et al., *Bioorg Med Chem Lett.* (2010) 20(22): 6680-4); A(16) and A(17(20)) analogues of A(16)-alphaxalone (see, e.g., Stastna, et al., *J Med Chem.* (2011) 54(11): 3926-34); neurosteroid analogs developed by CoCensys (now Purdue Neuroscience) (e.g., CCD-3693, Co2-6749 (a.k.a., GMA-839 and WAY-141839); neurosteroid analogs described in U.S. Pat. No. 7,781,421 and in PCT Patent Publications WO 2008/157460; WO 1993/003732; WO 1993/018053; WO 1994/027608; WO 1995/021617; WO 1996/016076; WO 1996/040043, as well as salts, hemisuccinates, nitrosylated, sulfates and derivatives thereof.

In various embodiments, the steroid or neurosteroid is not a sex hormone. In various embodiments, the steroid or neurosteroid is not progesterone.

As appropriate, the steroid or neurosteroid (e.g., allopregnanolone) may or may not be micronized. As appropriate, the steroid or neurosteroid (e.g., allopregnanolone) may or may not be enclosed in microspheres in suspension in the oil.

c. NMDA Receptor Antagonists

Illustrative NMDA receptor antagonists that find use include without limitation, e.g., dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine.tenocyclidine, methoxydine, tiletamine, xenon, neramexane, eliprodil, etoxadrol, dexoxadrol, WMS 2539, NEFA, remacemide, delucemine, 8A-PDHQ, aptiganel, 1 HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13. In some embodiments, the NMDA receptor antagonist is selected from the group consisting of ketamine, dextromethorphan, phencyclidine, CPPene (3-[(R)-2-carboxypiperazin-4-yl]-prop-2-enyl-1-phosphonic acid), selfotel, amantadine, dextrorphan, memantine, tiletamine, neramexane, cliprodil, remacemide, aptiganel, 1-Aminocyclopropanecarboxylic acid (ACPC), 7-Chlorokynurenate, DCKA (5,7-dichlorokynurenic acid), kynurenic acid, CP-101,606 (traxoprodil), AZD6765 (lanicemine) and GLYX-13. In some embodiments, the NMDA receptor antagonist is dizocilpine (MK-801).

5. Formulation and Administration

In various embodiments, one or more of the benzodiazepines and one or more neurosteroids are formulated for intramuscular, intravenous, subcutaneous, intrapulmonary and/or inhalational administration. In various embodiments, the benzodiazepines are formulated for delivery via an inhaler. In various embodiments other routes of delivery, described herein may be appropriate. Optionally a NMDA receptor antagonist is included in the compositions and/or co-administration.

Appropriate dosing will depend on the sire and health of the patient and can be readily determined by a trained clinician. Initial doses are low and then can be incrementally increased until the desired therapeutic effect is achieved with little or no adverse side effects. Determination of an effective amount for administration in a single dosage is well within the capability of those skilled in the art, especially in light of the detailed disclosure provided herein Generally, an efficacious or effective amount of the agents (e.g., one or more benzodiazepines and one or more neurosteroids, optionally including a NMDA receptor antagonist) is determined by first administering a low dose or small amount of the agent and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of agents of the present invention are described, for example, in *Goodman and Gilman's The Pharmacological Basis of Therapeutics*, 12th Edition, 2010, supra, in a Physicians' Desk Reference (PDR), 67$^{th}$ Edition, 2013; in *Remington: The Science and Practice of Pharmacy*, 21$^{st}$ Ed., 2005, supra, and in *Martindale: The Complete Drug Reference*, Sweetman, 2005, London: Pharmaceutical Press., and in Martindale, *Martindale: The Extra Pharmacopoeia*, 31st Edition, 1996, Amer Pharmaceutical Assn, each of which are hereby incorporated herein by reference.

In various embodiments, the agents (e.g., one or more benzodiazepines and one or more neurosteroids, optionally including a NMDA receptor antagonist) are nebulized. Methods and systems for intrapulmonary delivery of agents, e.g., benzodiazepines, are known in the art and find use. Illustrative systems for aerosol delivery of benzodiazepines by inhalation are described, e.g., in U.S. Pat. Nos. 5,497, 763; 5,660,166; 7,060,255; and 7,540,286; and U.S. Patent Publication Nos. 2003/0032638; and 2006/0052428, each of which are hereby incorporated herein by reference in their entirety for all purposes. Preferably, the agents (e.g., one or more benzodiazepines and one or more neurosteroids, optionally including a NMDA receptor antagonist) are nebulized without the input of heat.

For administration of the nebulized and/or aerosolized agents (e.g., one or more benzodiazepines and one or more neurosteroids, optionally including a NMDA receptor antagonist), the size of the aerosol particulates can be within a range appropriate for intrapulmonary delivery, particularly delivery to the distal alveoli. In various embodiments, the aerosol particulates have a mass median aerodynamic diameter ("MMAD") of less than about 5 µm, 4 µm, 3 µm, for example, ranging from about 1 µm to about 3 µm, e.g., from about 2 µm to about 3 µm, e.g., ranging from about 0.01 µm to about 0.10 µm. Aerosols characterized by a MMAD ranging from about 1 µm to about 3 µm can deposit on alveoli walls through gravitational settling and can be absorbed into the systemic circulation, while aerosols characterized by a MMAD) ranging from about 0.01 µm to 0.10 µm can also be deposited on the alveoli walls through diffusion. Aerosols characterized by a MMAD) ranging from about 0.15 µm to about 1 µm are generally exhaled. Thus, in various embodiments, aerosol particulates can have a MMAD ranging from 0.01 µm to about 5 µm, for example, ranging from about 0.05 µm to about 3 µm, for example, ranging from about 1 µm to about 3 µm, for example, ranging from about 0.01 µm to about 0.1 µm. The nebulized and/or aerosolized benzodiazepines can be delivered to the distal alveoli, allowing for rapid absorption and efficacy.

In various embodiments, the agents (e.g., one or more benzodiazepines and one or more neurosteroids, optionally including a NMDA receptor antagonist) are formulated in a solution comprising excipients suitable for aerosolized intrapulmonary delivery. The solution can comprise one or more pharmaceutically acceptable carriers and/or excipients. Pharmaceutically acceptable refers to approved or approvable by a regulatory agency of the Federal or a state government or listed in the U.S Pharmacopoeia or other generally recognized pharmacopoeia for use in animals, and more particularly in humans. Preferably, the solution is buffered such that the solution is in a relatively neutral pH range, for example, a pH in the range of about 4 to 8, for example, a pH in the range of about 5-7. In some embodiments, the benzodiazepine is formulated in a buffered solution, for example, phosphate-buffered saline.

In various embodiments, the agents (e.g., one or more benzodiazepines and one or more neurosteroids, optionally including a NMDA receptor antagonist) are prepared as a concentrated aqueous solution. Ordinary metered dose liquid inhalers have poor efficiency for the delivery to the deep lung because the particle size is not sufficiently small (Kim et al. 1985 *Am Rev Resp Dis* 132: 137-142; and Farr et al., 1995 *Thorax* 50:639-644) These systems are therefore used mostly for local delivery of drugs to the pulmonary airways. In addition, metered doses inhalers may not be able to deliver sufficient volumes of even a concentrated midazolam solution to produce the desired rapid antiseizure effect. Accordingly, in various embodiments, a metered doses inhaler is not used for delivery of the benzodiazepine, e.g., midazolam. In one embodiment a nebulization system with the capability of delivering <5 μm particles (e.g., the PARI LC Star, which has a high efficiency, 78% respirable fraction 0.1-5 μm, see, e.g., pari.com) is used for intrapulmonary administration. Electronic nebulizers which employ a vibrating mesh or aperture plate to generate an aerosol with the required particle size can deliver sufficient quantities rapidly and find use (See, e.g., Knoch and Keller, 2005 *Expert Opin Drug Deliv* 2: 377-390). Also, custom-designed hand-held, electronic nebulizers can be made and find use.

Aerosolized delivery of the agents (e.g., one or more benzodiazepines and one or more neurosteroids, optionally including a NMDA receptor antagonist) can allow for reduced dosing to achieve desired efficacy, e.g., in comparison to intravenous or intranasal delivery.

In various embodiments, the agents (e.g., one or more benzodiazepines and one or more neurosteroids, optionally including a NMDA receptor antagonist) are dissolved or suspended in a cyclodextrin. In varying embodiments, the cyclodextrin is an α-cyclodextrin, a β-cyclodextrin or a γ-cyclodextrin. In varying embodiments, the cyclodextrin is selected from the group consisting of hydroxypropyl-β-cyclodextrin, endotoxin controlled β-cyclodextrin sulfobutyl ethers, or cyclodextrin sodium salts (e.g., CAPTISOL®). Such formulations are useful for intramuscular, intravenous and/or subcutaneous administration.

In various embodiments, the agents (e.g., one or more benzodiazepines and one or more neurosteroids, optionally including a NMDA receptor antagonist) are dissolved or suspended in an oil that is edible and/or digestible by the subject, e.g., without undesirable side effects.

In various embodiments, the edible oil comprises one or more vegetable oils. In various embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof.

In some embodiments, the edible oil comprises one or more nut oils. In some embodiments, the nut oil is selected from the group consisting of almond oil, cashew oil, hazelnut oil, macadamia oil, mongongo nut oil, pecan oil, pine nut oil, pistachio oil, walnut oil, and mixtures thereof.

In some embodiments, the edible oil does not comprise castor oil. In some embodiments, the edible oil does not comprise peanut oil.

Generally, the oils used in the present compositions are isolated from the source, e.g., plant, and used without including further additives (e.g., surfactants, acids (organic or fatty), alcohols, esters, co-solvents, solubilizers, lipids, polymers, glycols) or processing. In various embodiments, the oil vehicle further comprises a preservative (e.g., vitamin E).

The oil-agents (e.g., one or more benzodiazepines and one or more neurosteroids, optionally including a NMDA receptor antagonist) compositions can be formulated for oral and/or transmucosal delivery using any method known in the art. In one embodiment, the oil-agents (e.g., one or more benzodiazepines and one or more neurosteroids, optionally including a NMDA receptor antagonist) composition is formulated in a capsule, e.g., for oral delivery.

a. Capsules

The capsule shells can be prepared using one or more film forming polymers. Suitable film forming polymers include natural polymers, such as gelatin, and synthetic film forming polymers, such as modified celluloses. Suitable modified celluloses include, but are not limited to, hydroxypropyl methyl cellulose, methyl cellulose, hydroxypropyl methyl cellulose acetate succinate, hydroxypropyl methyl cellulose phthalate, and cellulose acetate phthalate. Hard or soft capsules can be used to administer the hormone. Hard shell capsules are typically prepared by forming the two capsule halves, filling one of the halves with the fill solution, and then sealing the capsule halves together to form the finished capsule. Soft gelatin capsules are typically prepared using a rotary die encapsulation process as described below.

i. Gelatin Capsules

Gelatin is the product of the partial hydrolysis of collagen. Gelatin is classified as either Type A or Type B gelatin. Type A gelatin is derived from the acid hydrolysis of collagen while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid-processed gelatins form stronger gels than lime-processed gelatins of the same average molecular weight. The capsules can be formulated as hard or soft gelatin capsules.

ii. Non-Gelatin Capsules

Capsules can be prepared from non-gelatin materials, such as carrageenan or modified celluloses. Carrageenan is a natural polysaccharide hydrocolloid, which is derived from seaweed. It includes a linear carbohydrate polymer of repeating sugar units, without a significant degree of substitution or branching. Most, if not all, of the galactose units on a carrageenan molecule possess a sulfate ester group. There are three main types of carrageenan: kappa, iota and lambda; although minor forms called mu and nu carrageenan also exist.

iii. Shell Additives

Suitable shell additives include plasticizers, opacifiers, colorants, humectants, preservatives, flavorings, and buffering salts and acids, and combinations thereof.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

b. Enteric Capsules

Alternatively, the liquid fills can be incorporated into an enteric capsule, wherein the enteric polymer is a component of the capsule shell, as described in WO 2004/030658 to Banner Pharmacaps, Inc. The enteric capsule shell is prepared from a mass comprising a film-forming polymer, an acid-insoluble polymer which is present in an amount making the capsule resistant to the acid within the stomach, an aqueous solvent, and optionally, one or more plasticizers and/or colorants. Other suitable shell additives including opacifiers, colorants, humectants, preservatives, flavorings, and buffering salts and acids may be added.

i. Film-Forming Polymers

Exemplary film-forming polymers can be of natural or synthetic origin. Natural film-forming polymers include gelatin and gelatin-like polymers. Other suitable natural film-forming polymers include shellac, alginates, pectin, and zeins. Synthetic film-forming polymers include hydroxypropyl methyl cellulose, methyl cellulose, hydroxypropyl methyl cellulose acetate succinate, hydroxypropyl methyl cellulose phthalate, cellulose acetate phthalate, and acrylates such as poly (meth)acrylate. The weight ratio of acid-insoluble polymer to film-forming polymer is from about 15% to about 50% In one embodiment, the film forming polymer is gelatin.

ii. Acid-Insoluble Polymers

Exemplary acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (available under the tradename EUDRAGIT® from Rohm America Inc., Piscataway, N.J. as a powder or a 30% aqueous dispersion; or under the tradename EASTACRYL®, from Eastman Chemical Co. Kingsport. Tenn., as a 30% dispersion) in one embodiment, the acid-insoluble polymer is EUDRAGIT® L100, which is a methacrylic acid/methacrylic acid methyl ester copolymer. The acid-insoluble polymer is present in an amount from about 8% to about 20% by weight of the wet gelatin mass. The weight ratio of acid-insoluble polymer to film-forming polymer is from about 15% to about 50%.

iii. Aqueous Solvent

Hard and soft capsules are typically prepared from solutions or suspensions of the film forming polymer and the acid-insoluble polymer. Suitable solvents include water, aqueous solvents, and organic solvents. In one embodiment, the solvent is water or an aqueous solvent. Exemplary aqueous solvents include water or aqueous solutions of alkalis such as ammonia, sodium hydroxide, potassium hydroxide, ethylene diamine, hydroxylamine, tri-ethanol amine, or hydroalcoholic solutions of the same. The alkali can be adjusted such that the final pH of the gelatin mass is less than or equal to 9.0, preferably less than or equal to 8.5, more preferably less than or equal to 8.0. In one embodiment, the alkali is a volatile alkali such as ammonia or ethylene diamine. Upon drying of the finished capsule, the water content of the capsule is from about 2% to about 10% by weight of the capsule, preferably from about 4% to about 8% by weight of the capsule.

iv. Plasticizers

Exemplary plasticizers include glycerol, glycerin, sorbitol, polyethylene glycol, citric acid, citric acid esters such as triethylcitrate, polyalcohols with 3-6 carbons and combinations thereof. The plasticizer to polymer (film forming polymer plus acid-insoluble polymer) ratio is from about 10% to about 50% b of the polymer weight.

c. Methods of Manufacture i. Capsule Fill

The fill material is prepared by dissolving the steroid or neurosteroid (e.g., allopregnanolone) in the carrier containing a fatty acid solvent, such as oleic acid. The mixture of hormone and fatty acid may be heated to facilitate dissolution of the hormone. Upon cooling to room temperature and encapsulation, the solution remains a liquid. The fill is typically deacrated prior to encapsulation in a soft gelatin capsule. Additional excipients including, but not limited to, co-solvents, antioxidants may be added to the mixture of the hormone and fatty acid Again the mixture may be heated to facilitate dissolution of the excipients. The steroid or neurosteroid (e.g., allopregnanolone) is fully dissolved in the carrier of the present invention and remains so upon storage.

ii. Capsule Shell a. Gelatin or Non-Gelatin Capsules

The main ingredients of the capsule shell are gelatin (or a gelatin substitute for non-gelatin capsules), plasticizer, and purified water. The primary difference between soft and hard capsules is the amount of plasticizer present in the capsule shell.

Typical gel formulations contain (w/w) 40-50% gelatin, 20-30% plasticizer, and 30-40% purified water. Most of the water is subsequently lost during capsule drying. The ingredients are combined to form a molten gelatin mass using either a cold melt or a hot melt process. The prepared gel masses are transferred to preheated, temperature-controlled, jacketed holding tanks where the gel mass is aged at 50-60° C. until used for encapsulation.

i. Cold Melt Process

The cold melt process involves mixing gelatin with plasticizer and chilled water and then transferring the mixture to a jacket-heated tank. Typically, gelatin is added to the plasticizer at ambient temperature (18-22° C.). The mixture is cooked (57-95° C.) under vacuum for 15-30 minutes to a homogeneous, deaerated gel mass. Additional shell additives can be added to the gel mass at any point during the gel manufacturing process or they may be incorporated into the finished gel mass using a high torque mixer.

ii. Hot Melt Process

The hot melt process involves adding, under mild agitation, the gelatin to a preheated (60-80° C.) mixture of plasticizer and water and stirring the blend until complete melting is achieved. While the hot melt process is faster than the cold melt process, it is less accurately controlled and more susceptible to foaming and dusting.

h. Soft Capsules

Soft capsules are typically produced using a rotary die encapsulation process. The gel mass is fed either by gravity or through positive displacement pumping to two heated (48-65° C.) metering devices. The metering devices control the flow of gel into cooled (10-18° C.), rotating casting drums. Ribbons are formed as the cast gel masses set on contact with the surface of the drums.

The ribbons are fed through a series of guide rolls and between injection wedges and the capsule-forming dies A food-grade lubricant oil is applied onto the ribbons to reduce their tackiness and facilitate their transfer. Suitable lubricants include mineral oil, medium chain triglycerides, and soybean oil. Fill formulations are fed into the encapsulation machine by gravity. In the preferred embodiment, the soft capsules contain printing on the surface, optionally identifying the encapsulated agent and/or dosage.

Upon drying of the finished capsule, the water content of the capsule is from about 2% to about 10% by weight of the capsule, preferably from about 4% to about 8% by weight of the capsule.

c. Enteric Capsules

A method of making an enteric capsule shell is described in WO 2004/030658 to Banner Pharmacaps, Inc. The enteric mass is typically manufactured by preparing an aqueous solution comprising a film-forming, water soluble polymer and an acid-insoluble polymer and mixing the solution with one or more appropriate plasticizers to form a gelatin mass. Alternatively, the enteric mass can be prepared by using a ready-made aqueous dispersion of the acid-insoluble polymer by adding alkaline materials such as ammonium, sodium, or potassium hydroxides or other alkalis that will cause the acid-insoluble polymer to dissolve. The plasticizer-wetted, film-forming polymer can then be mixed with the solution of the acid-insoluble polymer. The mass can also be prepared by dissolving the acid-insoluble polymer or polymers in the form of salts of the above-mentioned bases or alkalis directly in water and mixing the solution with the plasticizer-wetted, film-forming polymer. The mass is cast into films or ribbons using heat controlled drums or surfaces. The fill material is encapsulated in a soft capsule using a rotary die. The capsules are dried under controlled conditions of temperature and humidity. The final moisture content of the shell composition is from about 2% to about 10% by weight of the capsule shell, preferably from about 4% to about 8% by weight by weight of the capsule shell.

Alternatively, release of the agents (e.g., one or more benzodiazepines and one or more neurosteroids, optionally including a NMDA receptor antagonist) from the capsule can be modified by coating the capsule with one or more modified release coatings, such as sustained release coatings, delayed release coatings, and combinations thereof.

The concentration of the agents (e.g., one or more benzodiazepines and one or more neurosteroids, optionally including a NMDA receptor antagonist) in the vehicle (e.g., cyclodextrin and/or edible oil) is preferably in unit dosage form. The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

In various embodiments, the benzodiazepines are administered at a dose that is less than about 10%, 15%, 25%, 50% or 75% of established doses for their administration for the prevention or mitigation of an epileptic seizure. In some embodiments, the benzodiazepine is administered at a dose in the range of about 0.05 mg/kg to about 1.0 mg/kg, for example, about 0.2 mg/kg to about 0.8 mg/kg, for example, about 0.05 mg/kg, 0.08 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, or 1.0 mg/kg. In some embodiments the benzodiazepine is administered at a dose in the range of about 10 µg/kg to about 80 µg/kg, for example, about 20 µg/kg to about 60 µg/kg, for example, about 25 g/kg to about 50 g/kg, for example, about 10 µg/kg, 15 µg/kg, 20 µg/kg, 25 µg/kg, 30 µg/kg, 35 µg/kg, 40 µg/kg, 45 µg/kg, 50 µg/kg, 60 µg/kg, 70 µg/kg, or 80 µg/kg. In some embodiments, the benzodiazepine is administered at a dose in the range of about 0.3 µg/kg to about 3.0 µg/kg. In varying embodiments, the benzodiazepine is administered at a dose that does not decrease blood pressure. When co-administered with one or more neurosteroids, the benzodiazepine can be co-administered at a dose that is less than about 10%, 15%, 259%, 50% or 75% of the aforementioned doses or at a dose that is less than about 10%, 15%, 25%, 50% or 75% of established doses for their administration for the prevention or mitigation of an epileptic seizure. When co-administered with one or more neurosteroids, the benzodiazepine can be co-administered at a dose that is less than about 10%, 15%, 25%, 50% or 75% of doses known to be efficacious via a selected route of administration (e.g., oral, intramuscular, intravenous, subcutaneous and/or intrapulmonary).

In various embodiments, the compositions are formulated for administration of about 5 mg/kg to about 50 mg/kg of the steroid or neurosteroid (e.g., allopregnanolone), e.g., about 5 mg/kg, 10 mg/kg, 15 mg/kg, 20 mg/kg, 25 mg/kg, 30 mg/kg, 35 mg/kg, 40 mg/kg, 45 mg/kg, or 50 mg/kg. When co-administered with one or more benzodiazepines, the steroid or neurosteroid (e.g., allopregnanolone) can be co-administered at a dose that is less than about 10%, 15%, 259%, 50% or 75% of the aforementioned doses or at a dose that is less than about 10%, 15%, 25%, 50% or 75% of established doses for their administration for the prevention or mitigation of an epileptic seizure. When co-administered with one or more benzodiazepines, the neurosteroid can be co-administered at a dose that is less than about 10%, 15%, 25%, 50% or 75% of doses known to be efficacious via a selected route of administration (e.g., oral, intramuscular, intravenous, subcutaneous and/or intrapulmonary).

6. Monitoring Efficacy

Co-administration of a benzodiazepine and a neurosteroid (optionally with an NMDA receptor antagonist) to a subject results in the prevention of the occurrence of an impending seizure and/or the rapid termination or abortion of a seizure in progress.

In various embodiments, efficacy can be monitored by the subject. For example, in a subject experiencing aura or receiving a warning from a seizure prediction device, the subject can self-administer via the intrapulmonary route a dose of the benzodiazepine. If the benzodiazepine is administered in an efficacious amount, the sensation of aura should subside and/or the seizure prediction device should no longer predict the imminent occurrence of an impending seizure. If the sensation of aura does not subside and/or the seizure prediction device continues to predict an impending seizure, a second dose of benzodiazepine can be administered.

In other embodiments, the efficacy is monitored by a caregiver. For example, in a subject experiencing the onset of a seizure or in situations where a seizure has commenced, the subject may require intrapulmonary administration of the benzodiazepine by a caregiver. If the benzodiazepine is administered in an efficacious amount, the seizure, along with the subject's symptoms of the seizure, should rapidly terminate or abort if the seizure does not terminate, a second dose of the benzodiazepine can be administered.

7. Kits

The pharmaceutical compositions and neurosteroid and benzodiazepine combinations can be provided in a kit. In certain embodiments, a kit of the present invention comprises one or more benzodiazepines and one or more neurosteroids in separate formulations. In varying embodiments, one or both of the benzodiazepine and the neurosteroid are provided in subtherapeutic doses or amounts in certain embodiments, the kits comprise one or more benzodiazepines and one or more neurosteroids within the same formulation. In varying embodiments, one or both of the benzodiazepine and the neurosteroid are provided in subtherapeutic doses or amounts. In certain embodiments, the kits provide the one or more benzodiazepines and one or more neurosteroids independently in uniform dosage formulations throughout the course of treatment. In varying embodiments, one or both of the benzodiazepine and the neurosteroid are provided in subtherapeutic doses or amounts. In certain embodiments, the kits provide the one or more benzodiazepines and one or more neurosteroids in graduated dosages over the course of treatment, either increasing or decreasing, but usually increasing to an efficacious dosage level, according to the requirements of an individual. In varying embodiments, one or both of the benzodiazepine and the neurosteroid are provided in subtherapeutic doses or amounts.

In some embodiments, the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam. In some embodiments, the benzodiazepine is selected from the group consisting of midazolam, lorazepam and diazepam. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the neurosteroid is allopregnanolone. In some embodiments, the kit comprises allopregnanolone and a benzodiazepine selected from the group consisting of midazolam, lorazepam, and diazepam.

In some embodiments, the kits further comprise a NMDA receptor antagonist. In some embodiments, the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), AP5 (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine.tenocyclidine, methoxydine, tiletamine, xenon, neramexane, eliprodil, etoxadrol, dexoxadrol, WMS 2539. NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13. In some embodiments, the NMDA receptor antagonist is selected from the group consisting of ketamine, dextromethorphan, phencyclidine, CPPene (3-[(R)-2-carboxypiperazin-4-yl]-prop-2-enyl-1-phosphonic acid), selfotel, amantadine, dextrorphan, memantine, tiletamine, neramexane, eliprodil, remacemide, aptiganel, 1-Aminocyclopropanecarboxylic acid (ACPC), 7-Chlorokynurenate, DCKA (5,7-dichlorokynurenic acid), kynurenic acid, CP-101,606 (traxoprodil), AZD6765 (lanicemine) and GLYX-13. In some embodiments, the NMDA receptor antagonist is dizocilpine (MK-801).

In some embodiments, one or both of the benzodiazepine and the neurosteroid is formulated for inhalational, intranasal or intrapulmonary administration. In some embodiments, one or both of the benzodiazepine and the neurosteroid is formulated for oral or parenteral delivery. In some embodiments, one or both of the benzodiazepine and the neurosteroid are formulated for a parenteral route selected from the group consisting of inhalational, intrapulmonary, intranasal, intramuscular, subcutaneous, transmucosal and intravenous. In some embodiments, the benzodiazepine is an agonist of the benzodiazepine recognition site on $GABA_A$ receptors and stimulates endogenous neurosteroid synthesis. In some embodiments, the neurosteroid is suspended or dissolved in a cyclodextrin (e.g., an α-cyclodextrin, a β-cyclodextrin or a γ-cyclodextrin). In varying embodiments, the neurosteroid is suspended or dissolved in a cyclodextrin selected from the group consisting of hydroxypropyl-β-cyclodextrin, endotoxin controlled β-cyclodextrin sulfobutyl ethers, or cyclodextrin sodium salts (e.g., CAPTISOL®). In some embodiments, the neurosteroid is suspended or dissolved in an edible oil. In some embodiments, the edible oil comprises one or more vegetable oils. In some embodiments, the vegetable oil is selected from the group consisting of coconut oil, corn oil, cottonseed oil, olive oil, palm oil, peanut oil, rapeseed oil, canola oil, safflower oil, sesame oil, soybean oil, sunflower oil, and mixtures thereof. In some embodiments, the edible oil is canola oil. In some embodiments, the edible oil comprises one or more nut oils. In some embodiments, the nut oil is selected from the group consisting of almond oil, cashew oil, hazelnut oil, macadamia oil, mongongo nut oil, pecan oil, pine nut oil, pistachio oil, walnut oil, and mixtures thereof.

EXAMPLES

The following examples are offered to illustrate, but not to limit the claimed invention.

Example 1

Tetramethylenedisulfotetramine Alters Ca2+ Dynamics in Cultured Hippocampal Neurons: Mitigation by NMDA Blockade and $GABA_A$ Receptor Positive Modulation Materials and Methods Materials Fetal bovine serum and soybean trypsin inhibitor were obtained from Atlanta Biologicals (Norcross, Ga.). DNase, poly-L-lysine, cytosine arabinoside, (−)-5-methyl-10,11-dihydro-5H-dibenzo[a,d]cyclohepten-5,10-imine maleate (MK-801), Hydroxypropyl-β-cyclodextran, and (3,5-dimethyl 2,6-dimethyl-4-(2-nitrophenyl)-1,4-dihydropyridine-3,5-dicarboxylate (nifedipine) were from Sigma-Aldrich (St. Louis, Mo.). The Ca2| fluorescence dye Fluo-4, Pluronic F-127 and Neurobasal medium were purchased from Life Technology (Grand Island, N.Y.). Tetramethylenedisulfotetramine (TETS) was synthesized as described previously (Zolkowska et al., 2012). Diazepam was from Western Medical Supply (Arcadia, Ca.). Allopregnanolone (3α-hydroxy-5α-pregnan-20-one; >99%) was provided by M A. Rogawski.

Primary Cultures of Hippocampal Neurons.

Animals were treated humanely and with regard for alleviation of suffering according to protocols approved by the Institutional Animal Care and Use Committee of the University of California, Davis. Hippocampal neuron cultures were dissociated from hippocampi dissected from C57BL/6J mouse pups at postnatal day 0-1 and maintained in Neurobasal complete medium [Neurobasal medium supplemented with NS21, 0.5 mM L-glutamine, HEPES] with 5% fetal bovine serum. For Ca2| imaging studies using FLIPR, dissociated hippocampal cells were plated onto poly-L-lysine coated clear-bottom, black wall, 96-well imaging plate (BD, Franklin Lakes, N.J., USA) at a density of $0.8 \times 10^5$/well. For microelectrode array (MEA) experiments, 120 µl of cell suspension at a density of $1.5 \times 10^6$ cells/ml were added to a 12-well Maestro plate (Axion Biosystems, Atlanta, Ga.). After 2 h incubation, a volume of 1.0 ml of serum-free Neurobasal complete medium was added to each well. The medium was changed twice a week by replacing half volume of culture medium with scrum-free Neurobasal complete medium. The neurons were maintained at 37° C. with 5% CO2 and 95% humidity.

Measurement of Synchronous Intracellular Ca2 Oscillations.

Hippocampal neurons between 13-17 days in vitro (DIV) were used to investigate how TETS alters synchronous Ca2· oscillations that normally occur in healthy neurons at this developmental stage. This method permits simultaneous measurements of intracellular Ca2· transients in a 96-well format as described as previously (Cao et al., 2010). Baseline recording were acquired in Locke's buffer (8.6 mM HEPES, 5.6 mM KCl, 154 mM NaCl, 5.6 mM glucose, 1.0 mM $MgCl_2$, 2.3 mM $CaCl_2$, and 0.0001 mM glycine, pH 7.4) for 10 min followed by addition of TETS and/or pharmacological agents using a programmable 96-channel pipetting robotic system, and the intracellular Ca2– was monitored for an additional 30 min. Unless otherwise indicated, pharmacological interventions were introduced 10 min prior to TETS. TETS triggered an immediate rise in [Ca2·]i that was analyzed by quantifying the Area Under the Curve (AUC; in arbitrary fluorescence units) of the Fluo-4 fluorescence units for a duration of 5 min following TETS addition. TETS also altered the frequency and amplitude of neuronal synchronous Ca2| oscillations, which were analyzed during the 10 min period after addition of TETS.

MEA Recording.

All MEA recordings were conducted at 37° C. in culture medium without perfusion using a 12-well Maestro system (Axion BioSystems, Atlanta, Ga.). Each well contains 64 electrodes (30 µm diameter) in an 8×8 grid with inter-electrode spacing of 200 µm. Before recording basal electrical activity, the cultures were equilibrated in freshly prepared, pre-warmed neurobasal complete medium for 1 h. The 12-well Maestro plates were loaded onto a temperature regulated headstage containing the recording amplifier and raw extracellular electrical signals were acquired using Axis software (Axion BioSystems, Atlanta, Ga.). Signals from the amplifier were digitized at a rate of 25 KHZ, and filtered using Butterworth Band-pass filter (cutoff frequency of 300 Hz). The Axis software was used to detect spontaneous events that exceeded a threshold of six times of the noise. Raster plot and spike rate analysis data were performed by exporting the raw data to the NeuroExplorer software (version 4.0, NEX Technologies, Littleton, Mass.).

Data Analysis. Graphing and statistical analysis were performed using GraphPad Prism software (Version 5.0, GraphPad Software Inc., San Diego, Calif.). EC50 values were determined by non-linear regression using a three-parameter logistic equation. Statistical significance between different groups was calculated using Student's 1-test or by an ANOVA and, where appropriate, a Dunnett's Multiple Comparison Test; p values below 0.05 were considered statistically significant.

Results

Effects of TETS on Ca2 · Oscillations in Primary Cultured Hippocampal Neurons.

Figure 1A:
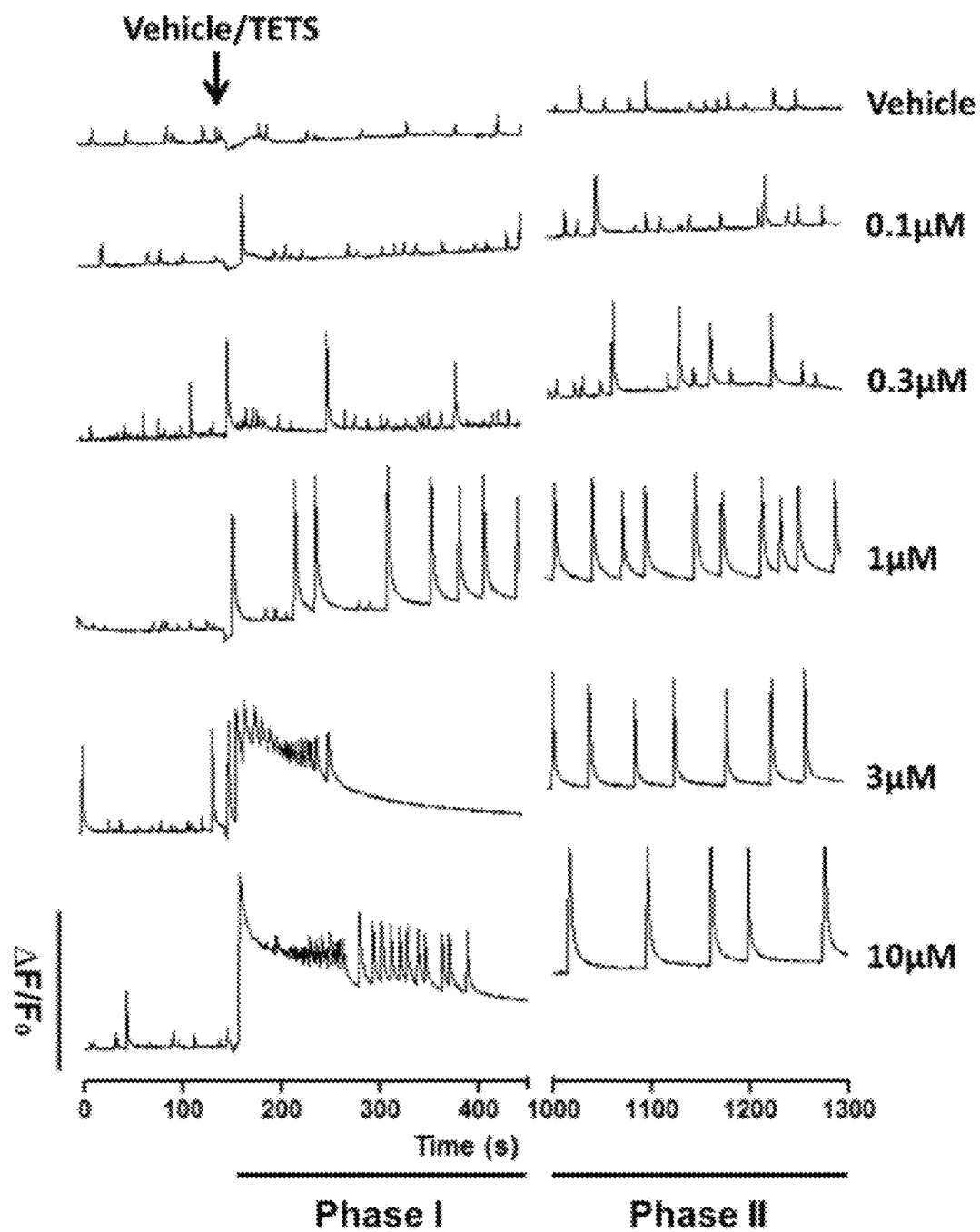
FIGS. 1A-D illustrate TETS-induced Ca2− dysregulation in hippocampal neurons. (A) Representative traces showing how acute exposure to TETS (0.1-10 μM) influences Ca2· fluctuations in hippocampal neurons 13-17 DIV. Note that neurons exhibit spontaneous synchronous Ca2| oscillations at this developmental stage indicative of functional network connectivity. The effects of TETS were analyzed in the initial 5 min following addition (Phase I) and in the subsequent 10 min (Phase II). In Phase I, the integrated intracellular Ca2+ level increased in a concentration-dependent fashion (B), and there was a plateau response at higher concentrations (3, 10 μM) that decayed slowly over the 5 min period. In Phase II, there was a concentration-dependent reduction in the frequency and an increase in the amplitude of the spontaneous synchronized Ca2− oscillations (C,D). The traces shown for Phase II are representative samples of the 10 min Phase II period. This experiment was repeated three times with similar results.
Figure 1B:
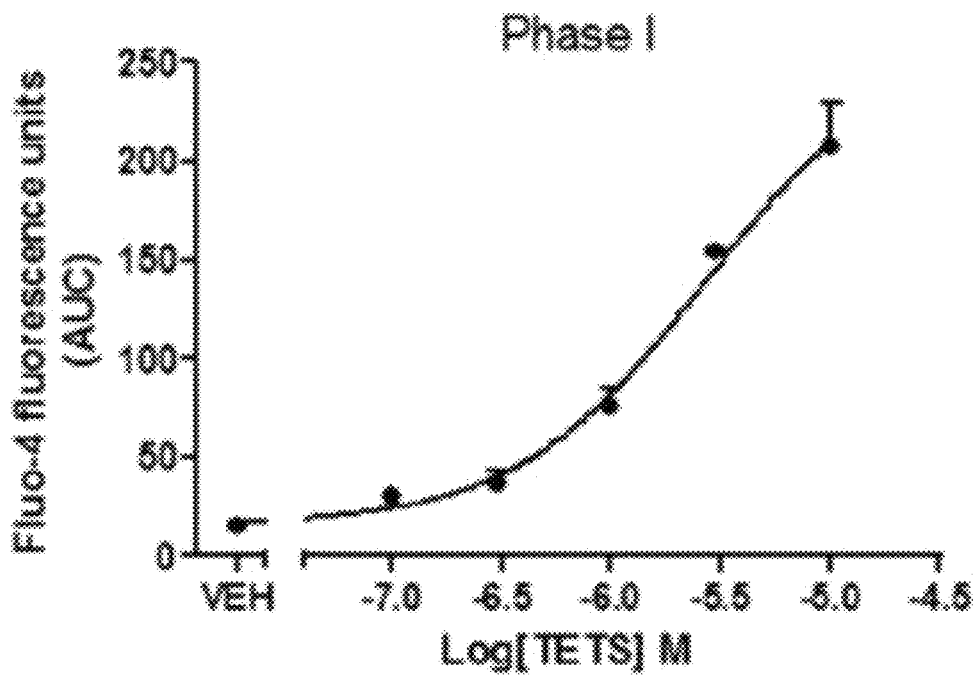
Figure 1C:
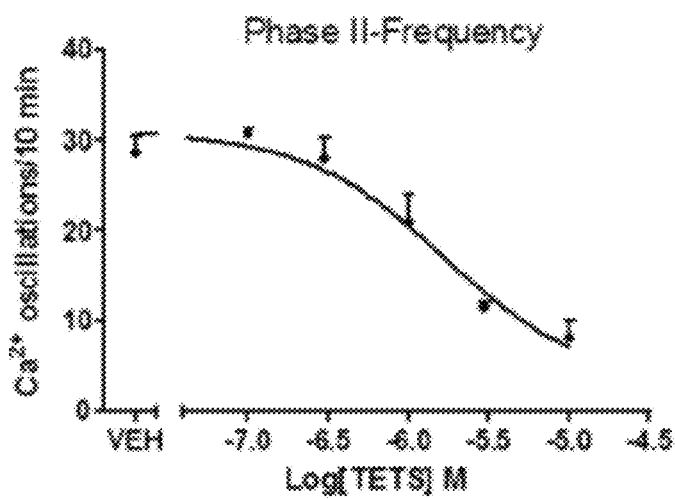
Figure 1D:
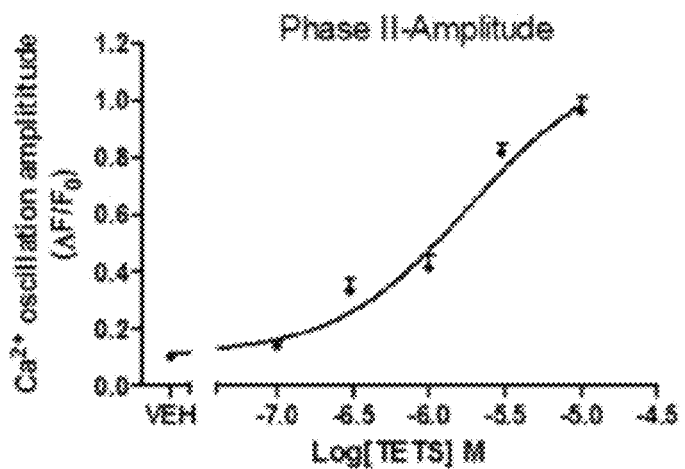
Figure 2:
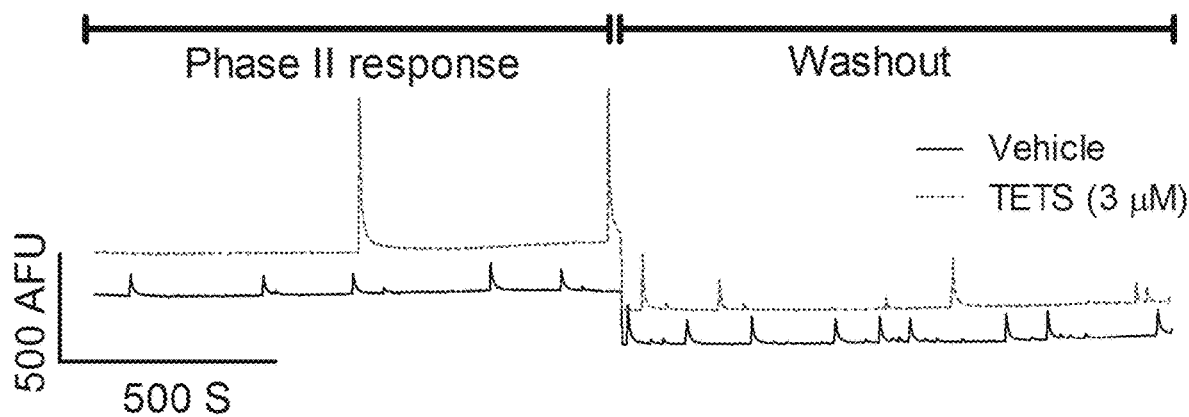
FIG. 2 illustrates reversal of TETS-induced Phase II effects after washout of TETS Traces show synchronized Ca2− oscillations that are reduced in frequency and increased in amplitude in the presence of TETS. The dotted red line is a representative trace before ("Phase II response") and after TETS ("Washout"). The solid black line is a representative recording from a control experiment in which the culture was treated with vehicle and subjected to the same washout procedure.
Figure 3A:
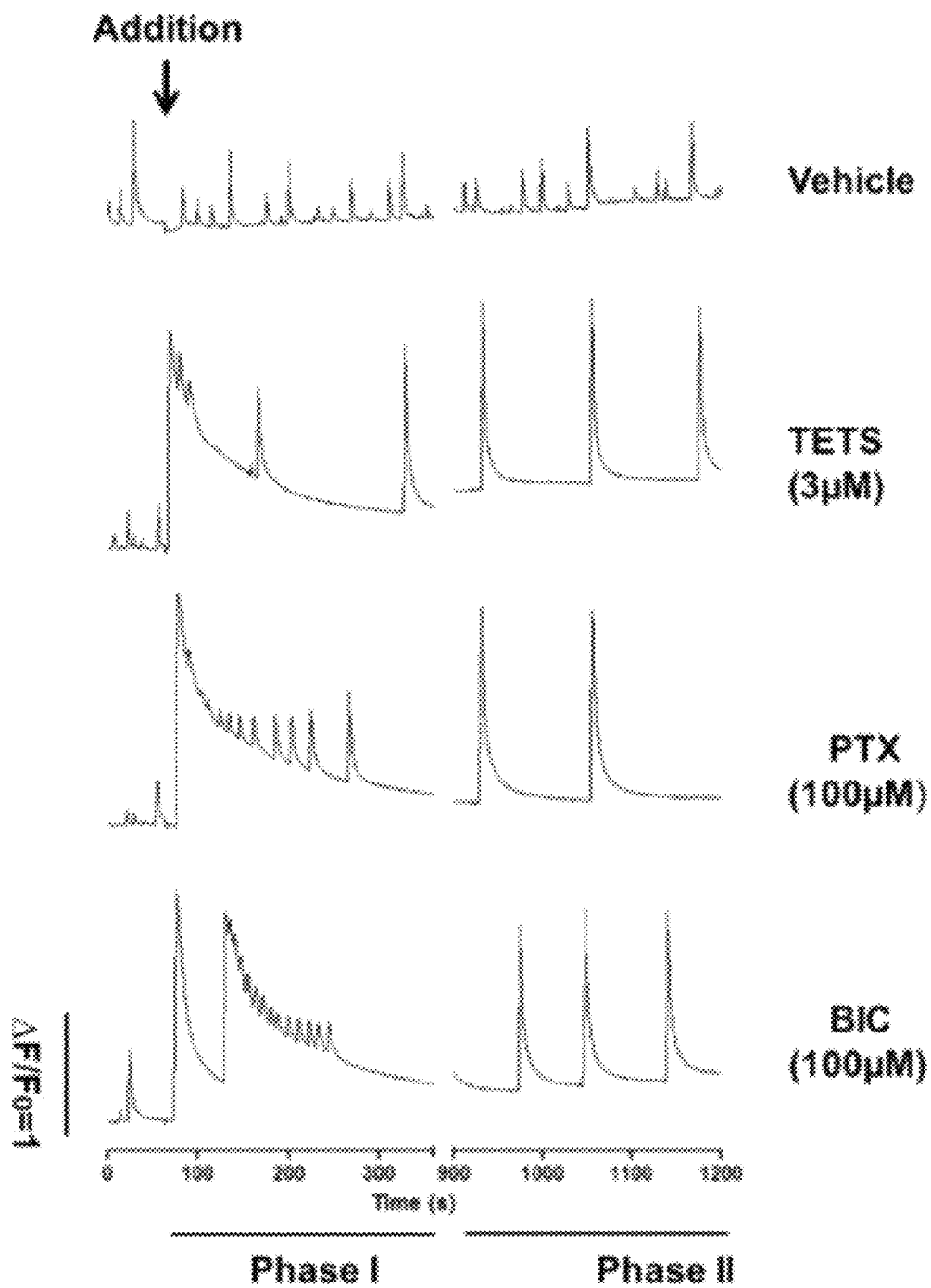
FIGS. 3A-D illustrate TETS, picrotoxin, and bicuculline trigger similar neuronal Ca2+ dysregulation. (A) Representative traces from experiments comparing the effects of TETS (3 μM), picrotoxin (100 μM), and bicuculline (100 μM) on Ca2+ fluctuations. The three agents produce similar acute elevation of the integrated Ca2+ level (B) with plateau responses in Phase I, and they decreased the oscillator) frequency (C) while increasing the amplitude of Ca2+ transients in Phase II (D). **, $p<0.01$, inhibitors vs. control, data were pooled from three experiments performed at least in duplicate.
Figure 3B:
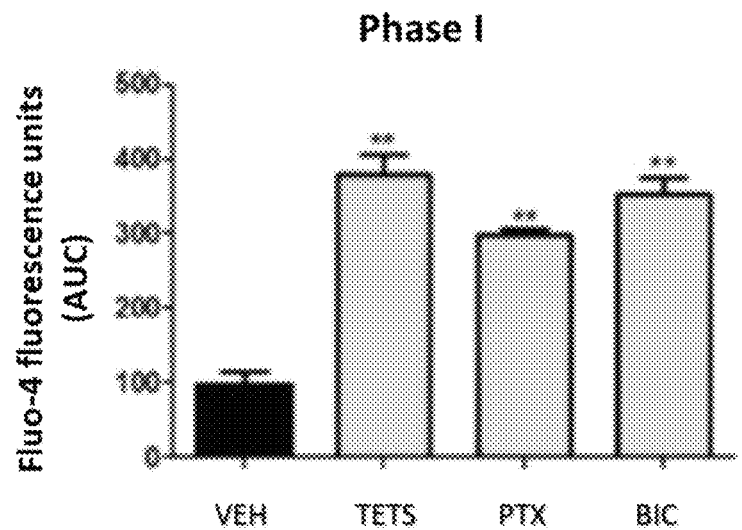
Figure 3C:
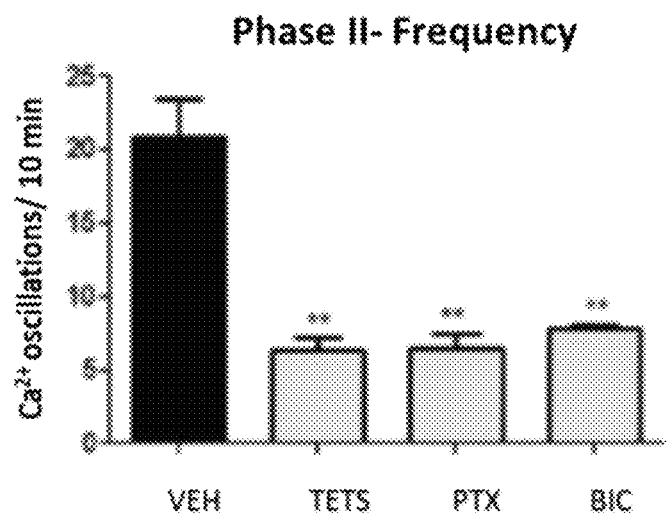
Figure 3D:
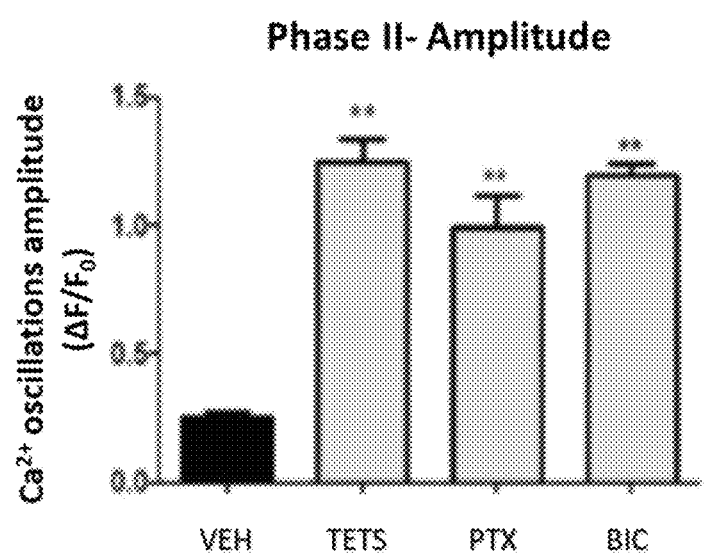

Cultured hippocampal neurons (13-17 DIV) exhibit spontaneous synchronous Ca2– oscillations whose frequency and amplitude can be quantitatively assessed in real time using FLIPR® (FIG. 1A). Addition of DMSO vehicle had no significant effect on the properties of the synchronous Ca2· oscillations during the 5 min Phase I period or the 10 min Phase II period (FIG. 1A, top trace). By contrast, exposure of the neurons to TETS caused an immediate increase in the amplitude of the oscillations and at higher concentrations (3 and 10 µM) a sustained plateau response that decayed slowly over the 5 min Phase I period. The integrated Ca2– signal (area under the curve: AUC) during the Phase I period exhibited a concentration-dependent increase, with an EC50 value of 2.7 µM [95% confidence interval (95% CI): 1.4-5.2 µM] (FIG. 1B). During Phase II, TETS caused a concentration-dependent decrease in the frequency of the synchronous Ca2+ oscillations with an EC50 value of 1.7 µM (95% CI 0.69-4.12 µM; FIG. 1C) Along with the reduction in frequency, TETS increased the mean Ca2· oscillation amplitude with an EC50 value of 1.8 µM (95% CI: 1.12-2.80 µM; FIG. 1D). TETS modestly prolonged the mean duration of individual Ca2· transients compared to that measured from vehicle-exposed control neurons. TETS-induced phase II Ca2| responses (both frequency and amplitude) were reversible (FIG. 2)

For comparison, we studied the influence of picrotoxin (PTX; 100 µM), a noncompetitive blocker of $GABA_A$ receptor and bicuculline (100 µM), a competitive antagonist of $GABA_A$ receptors on the Ca2| dynamics. Both antagonists elicited similar Phase I and Phase II responses as TETS (FIG. 3).

TETS Enhances Neuronal Electric Network Activity in Primary Cultured Hippocampal Neurons.

Figure 4A:
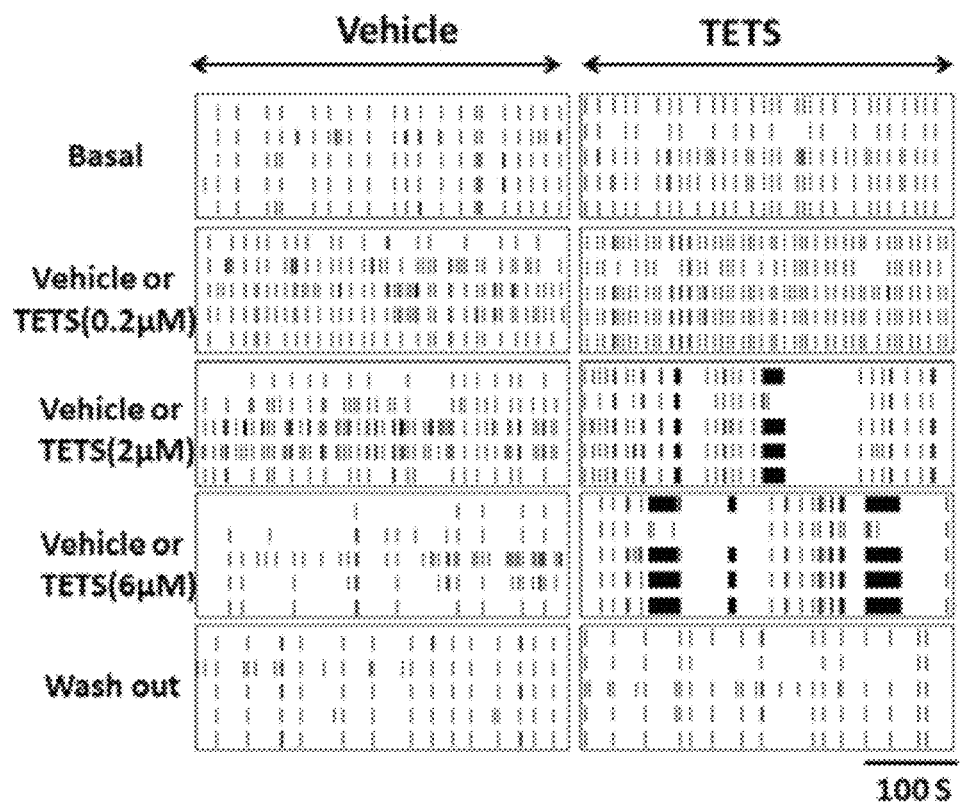
FIGS. 4A-B illustrate TETS-reversibly alters spontaneous electrical discharges in hippocampal neurons. (A) Representative raster plots of neuronal discharges before, during and after exposure to vehicle (DMSO) (left panels) or TETS (right panels). Neuronal network activity was stable for up to 60 min in the absence or presence of vehicle control. TETS solutions of increasing concentration were added serially to the wells. After recording for 10 min, the solution was removed and replaced by a higher concentration or by vehicle (wash out). TETS concentrations of 2 and 6 μM caused a clustered burst discharge pattern and increased the overall discharge frequency (B). This experiment was repeated three times each performed in duplicate with similar results. *, $p<0.05$, **, $p<0.01$, TETS vs. basal.
Figure 4B:
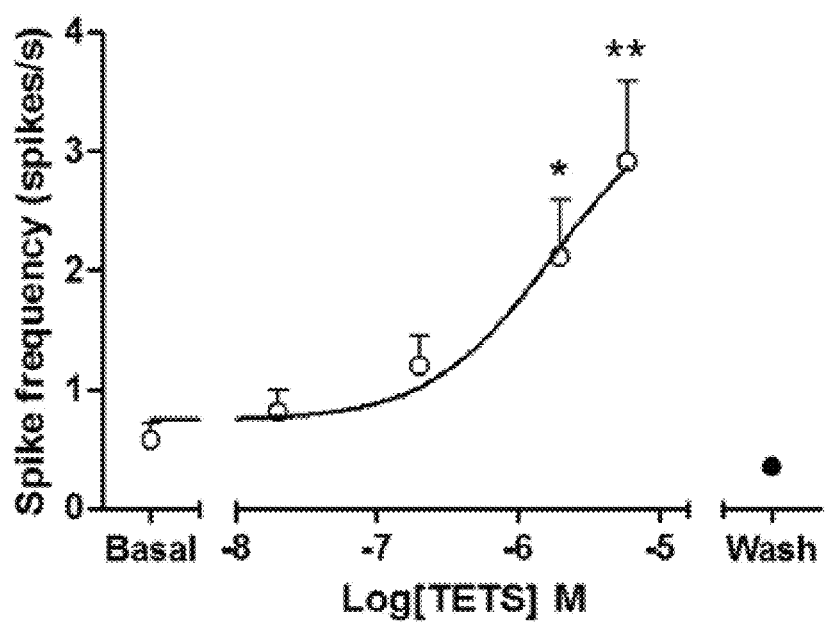
Figure 5A:
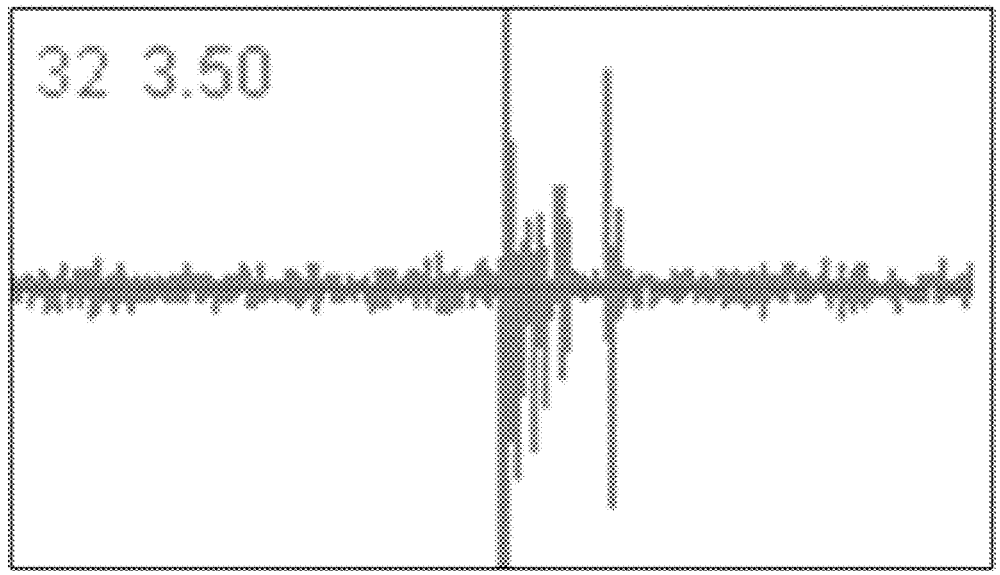
FIGS. 5A-B illustrates TETS-induced a pattern of clustered electrical burst firing in hippocampal neuronal cell cultures at 14 days in vitro. Representative traces of neuronal electrical firing from an MEA recording before (A) and after (B) addition of TETS (6 μM). The software only allows a display of 200 ms; the actual total period of clustered bursts after TETS treatment often lasted up to 10 s (see FIG. 3A, right panel, 4th row).
Figure 5B:
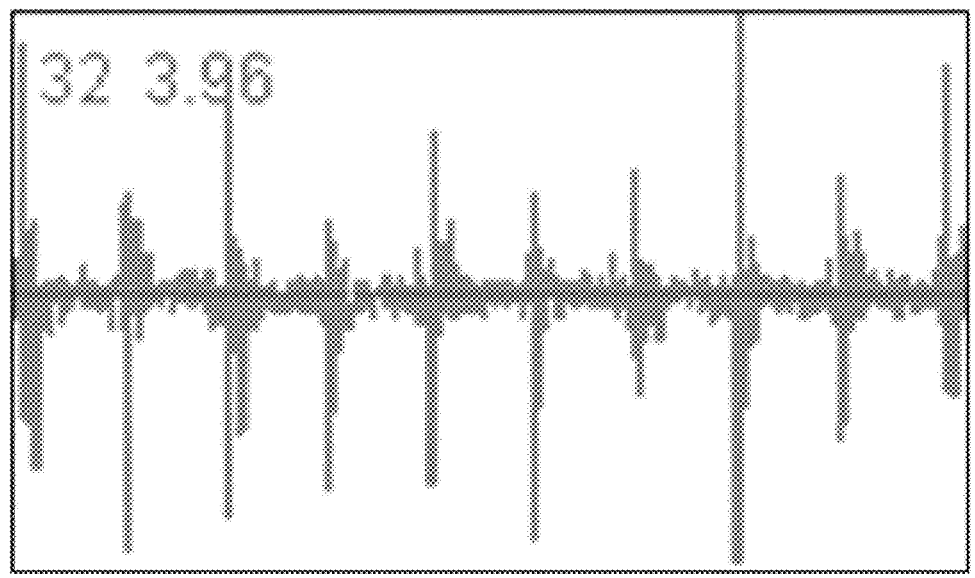

Extracellular recordings of electrical activity from multiple sites within the neuronal cultures at a high spatial resolution provide a robust measure of network activity and connectivity (Johnstone et al., 2010) After recording the basal electrical activity for 10 min, increasing concentrations of TETS were serially introduced into the wells. The recording was continued for 10 min at each TETS concentration A control well was simultaneously recorded following introduction of DMSO vehicle (0.01-0.1%). Basal recordings for up to 60 min showed that network firing activity was stable in the absence or presence of DMSO vehicle control (FIG. 4A, left panel). Exposure to TETS concentrations of 2 µM and greater produced a dramatic change in discharge pattern. Events became more highly clustered (FIG. 4A, right panel and FIG. 5) and the duration of clustered bursts induced by 6 μM TETS can last up to 10 s (FIG. 4A, right panel, 4th row). There was an overall increase in the discharge rate (FIG. 4B.) After washout of TETS, the neuronal network firing recovered to basal conditions.

NMDA Receptors, but not L-type Ca2· Channels Are Required for TETS—Induced Ca2· Dysregulation.

Figure 6A:
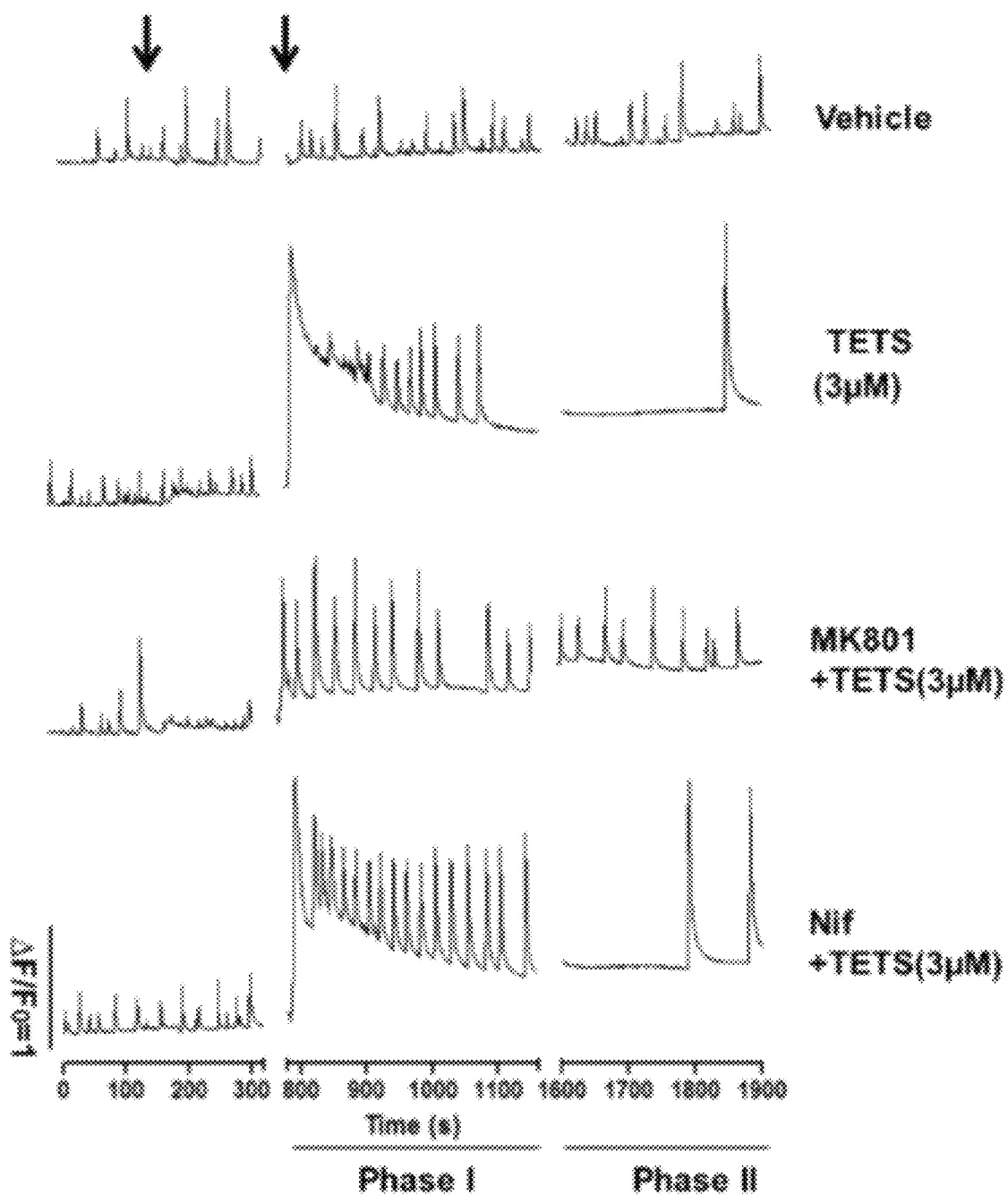
FIGS. 6A-D illustrate MK-801, but not nifedipine, partially mitigates TETS (3 μM)-induced neuronal Ca2+ dysregulation. (A) Representative traces illustrating effects of pre-exposure to MK-801 and nifedipine on TETS-induced Ca2+ dysregulation. (B) Effects of MK-801 (MK) and nifedipine (NIF) on TETS-induced increase in integrated Ca2+ levels in Phase I. (C,D) Effects of MK-801 and nifedipine on the TETS-induced synchronous Ca2+ transient oscillation frequency decrease (C) and amplitude increase (D) in Phase II. **, $p<0.01$, TETS vs. vehicle control, ##, $p<0.01$, MK-801+TETS vs TETS, n=6 pooled from two experiments.
Figure 6B:
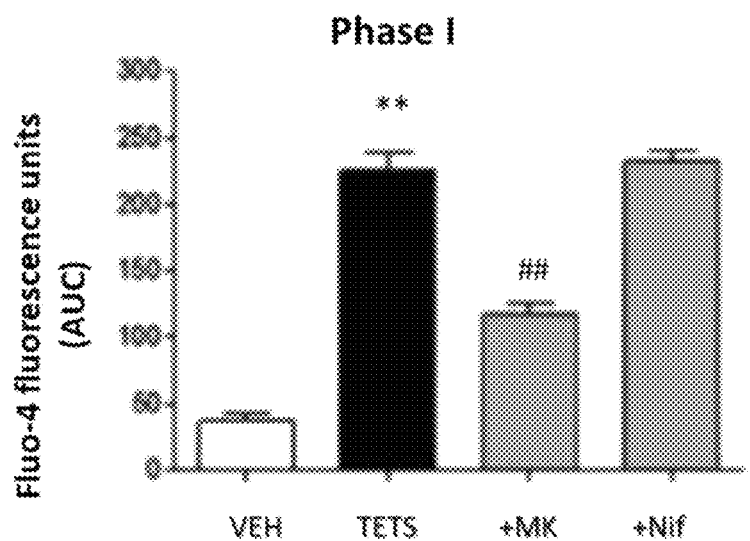
Figure 6C:
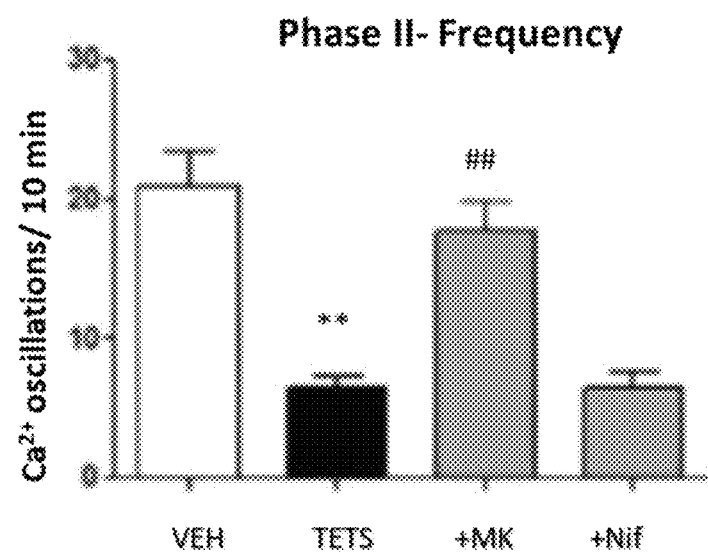
Figure 6D:
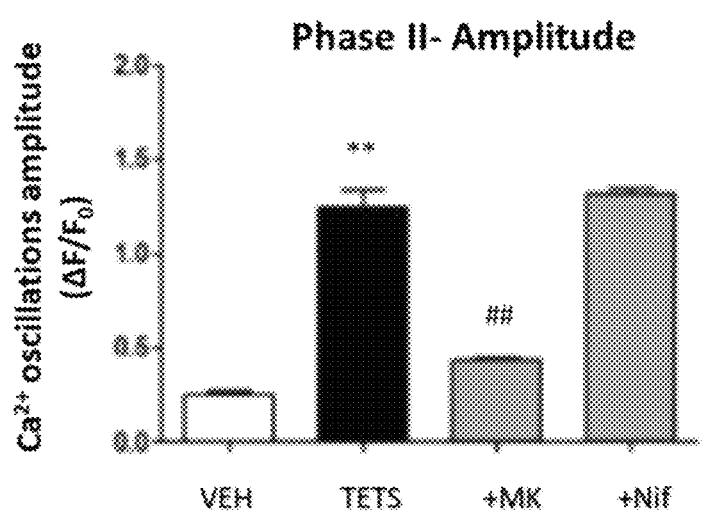

We next examined the possible involvement of NMDA receptors and L-type Ca2+ channels in the effects of TETS on Ca2− dynamics. Preincubation of neuronal cultures for 10 min with MK-801 (1 μM), an NMDA receptor blocker, attenuated both Phase I and Phase II effects of TETS (FIG. 6B-D) MK-801 slightly suppressed basal Ca2· oscillations, which is consistent with an earlier report (Tanaka et al., 1996). By contrast, nifedipine (1 μM), which inhibits L-type voltage activated Ca2| channels, was without effect on TETS-induced Phase I or Phase II Ca2| responses (FIG. 6B-D). These results indicate that NMDA receptors but not L-type Ca2· channels are required for the effects of TETS on Ca2| fluctuations.

Diazepam and Allopregnanolone Partially Mitigate TETS-Induced Ca2· Dysregulation.

Figure 7A:
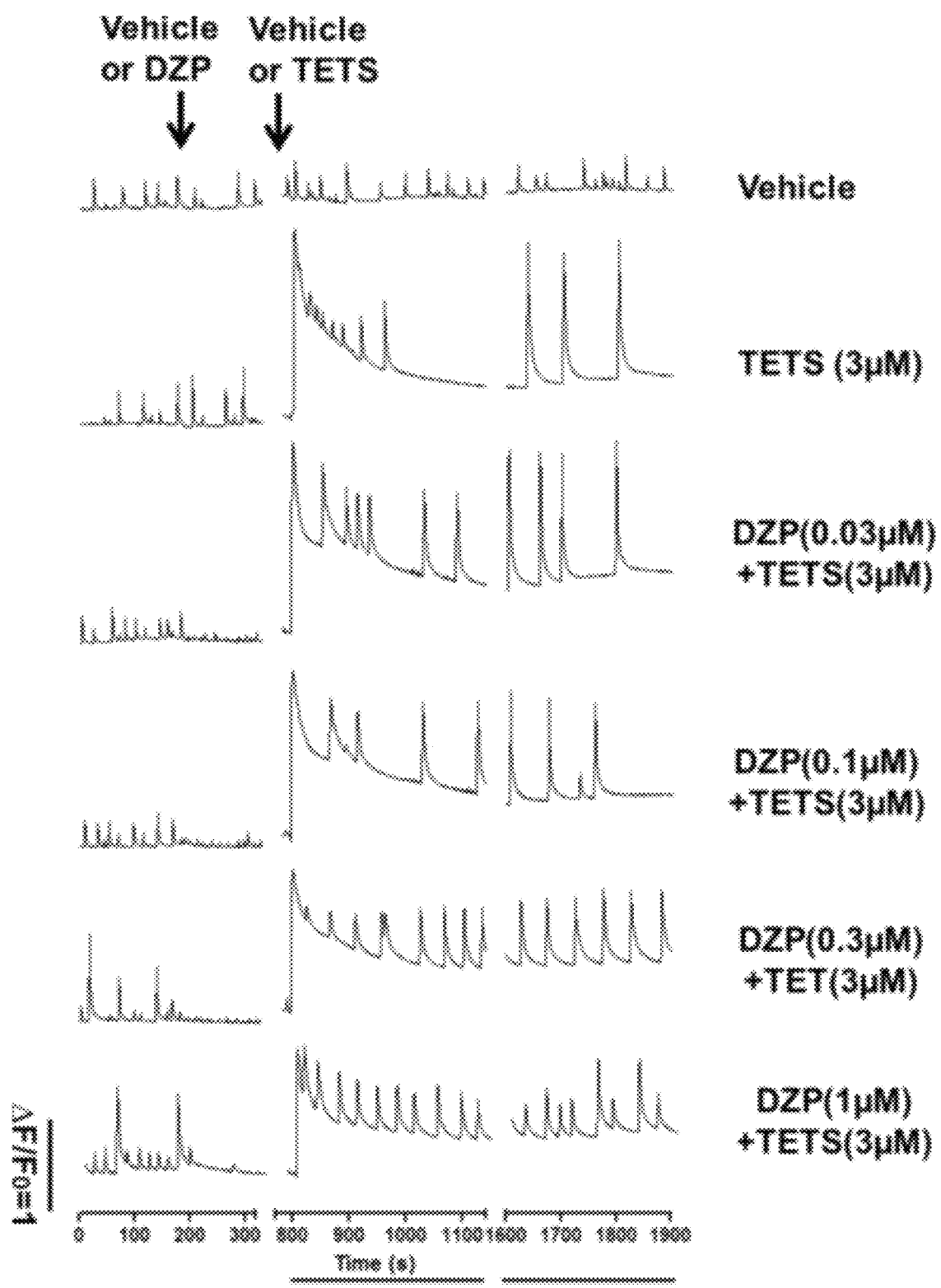
FIGS. 7A-D Diazepam partially mitigates TETS-induced neuronal Ca2+ dysregulation. (A) Representative traces illustrating effects of pre-exposure to increasing concentrations of diazepam (0.03-1 μM) on TETS-induced Ca2+ dysregulation. (B) Effect of diazepam (DZP) on TETS-induced increase in integrated Ca2+ levels in Phase I. (C,D) Effect of diazepam on the TETS-induced synchronous Ca2+ transient oscillation frequency decrease (C) and amplitude increase (D) in Phase II. **, $p<0.01$, TETS vs. vehicle control, #, $p<0.05$, ##, $p<0.01$, diazepam+TETS vs. TETS, n=6 pooled from two experiments.
Figure 7B:
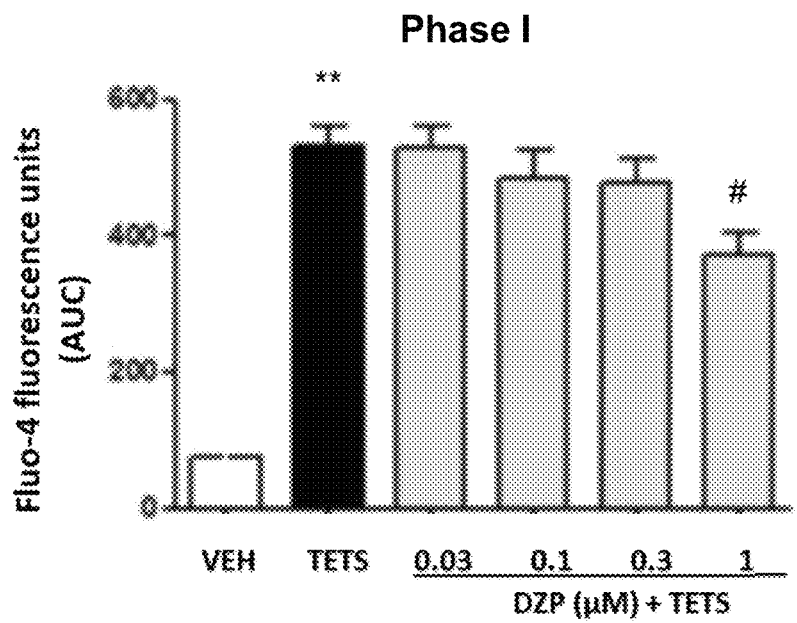
Figure 7C:
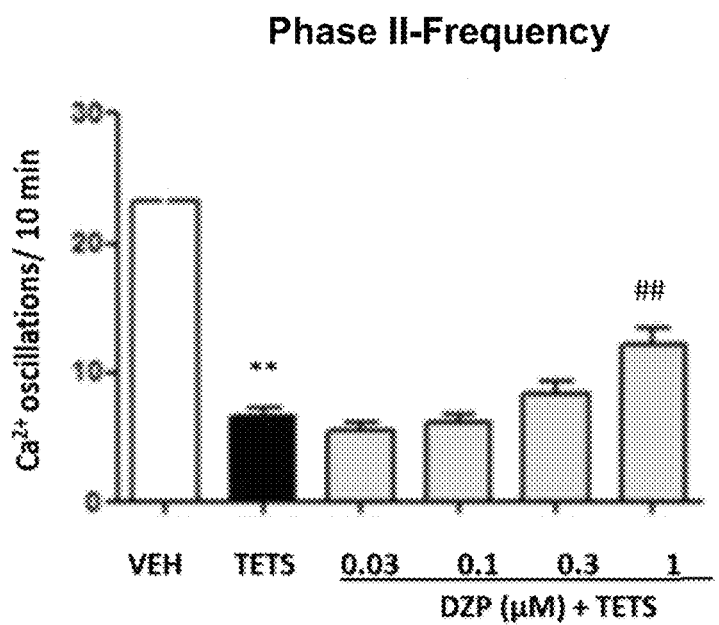
Figure 7D:
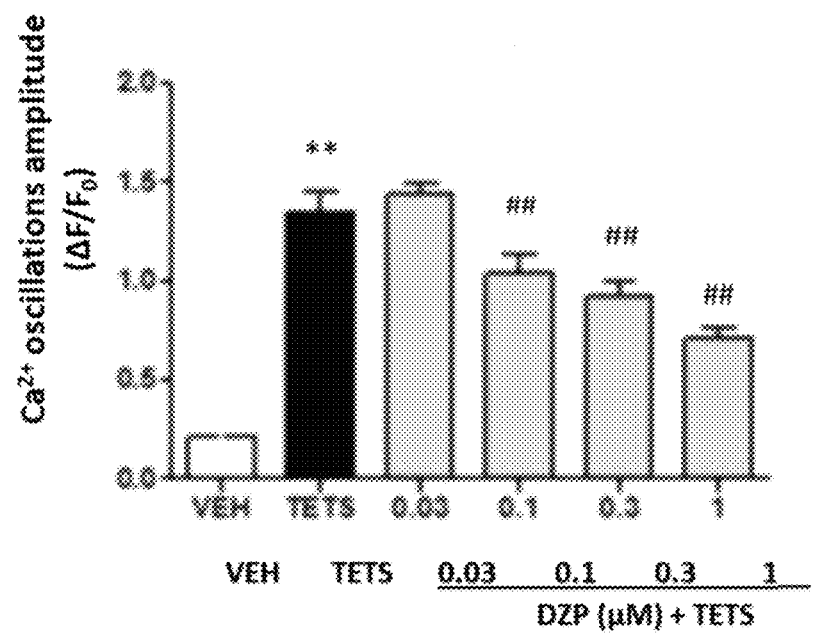
Figure 8A:
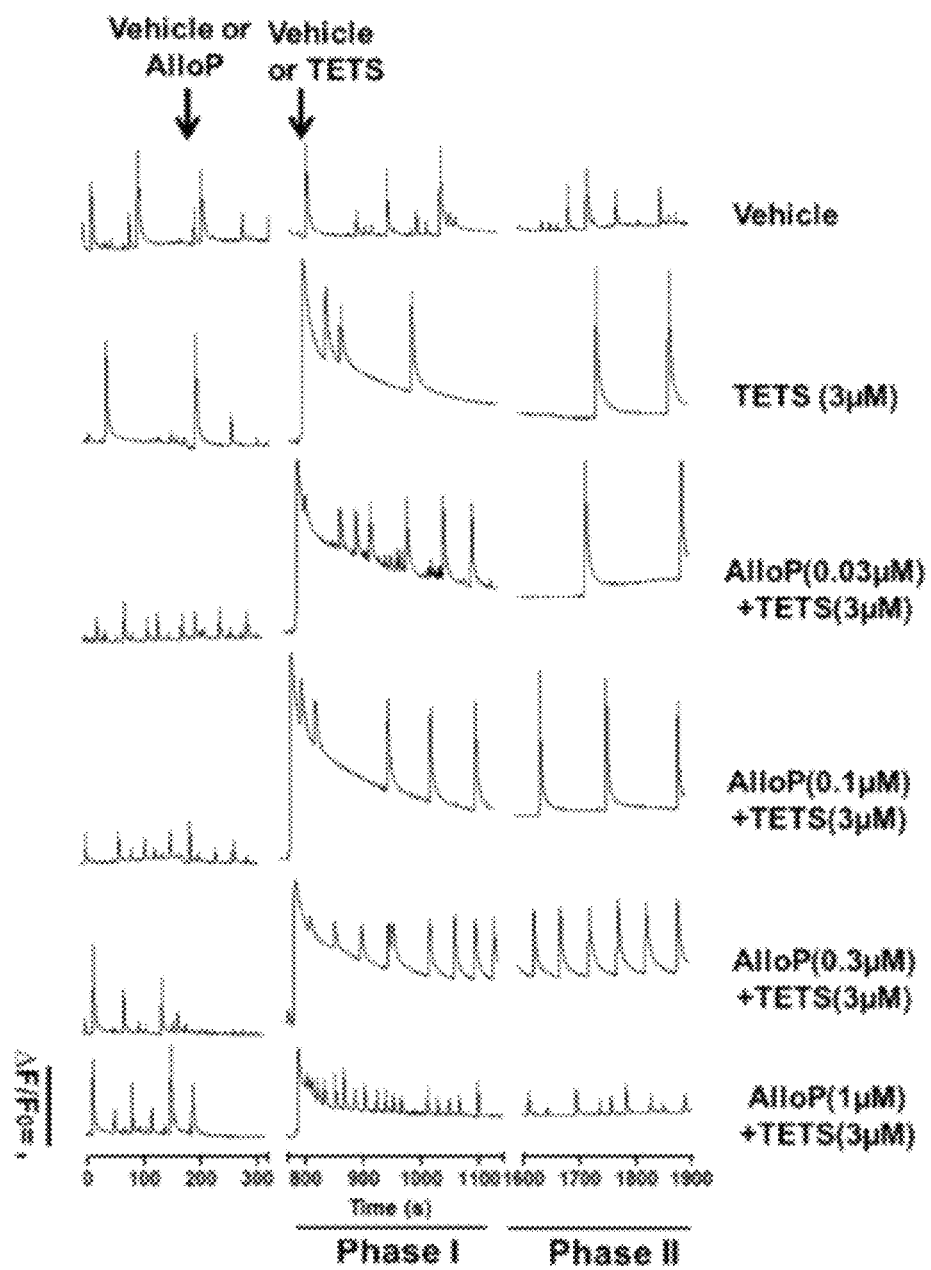
FIGS. 8A-D illustrate allopregnanolone partially mitigates TETS-induced neuronal Ca2+ signaling dysregulation.
Figure 8B:
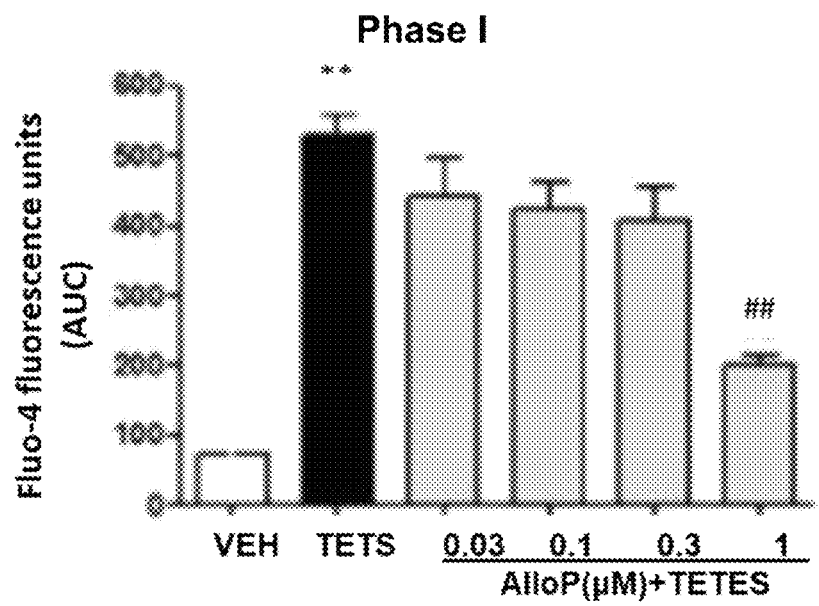
Figure 8C:
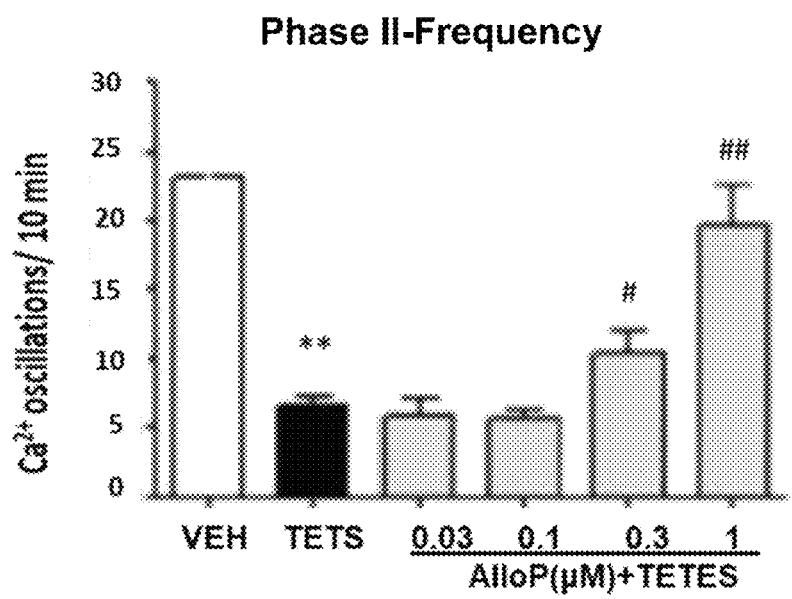
Figure 8D:
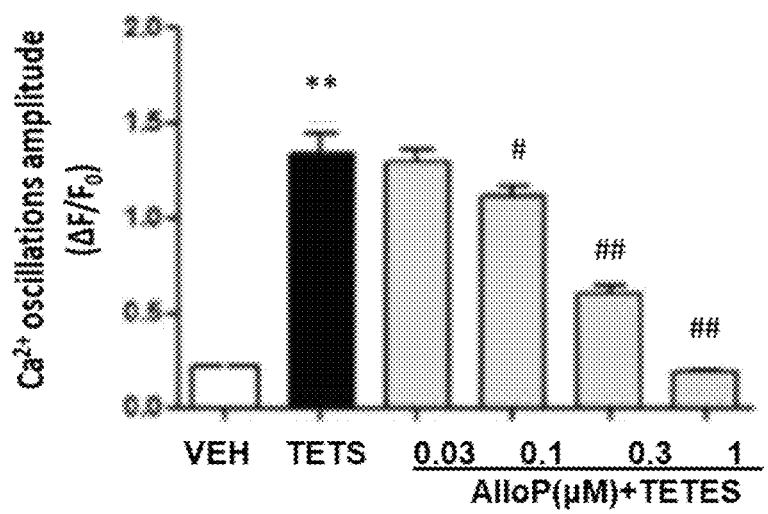
Figure 9A:
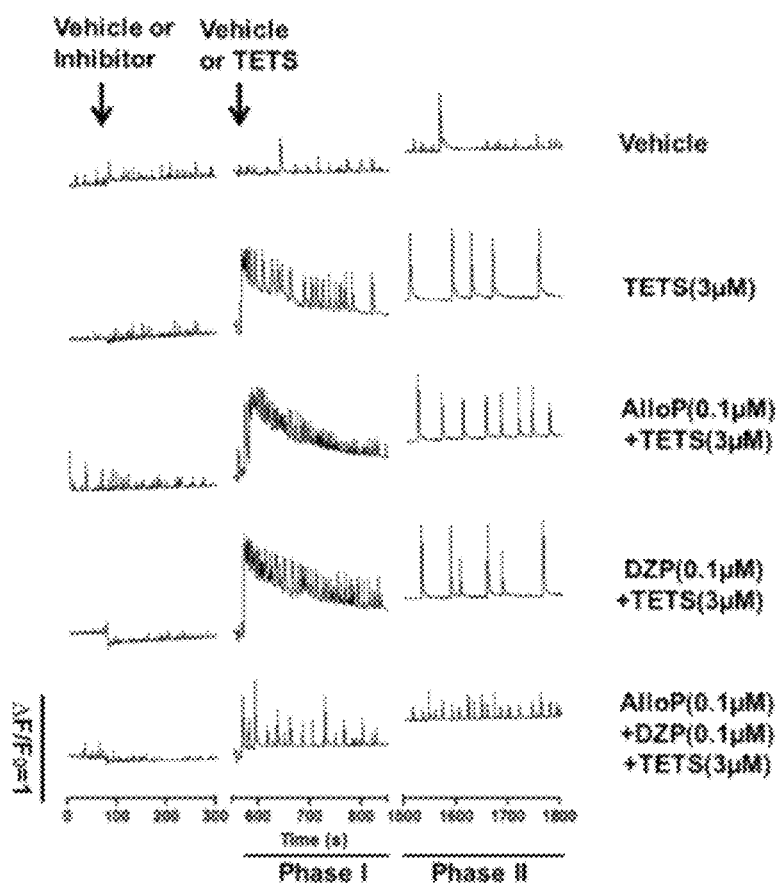
Figure 9B:
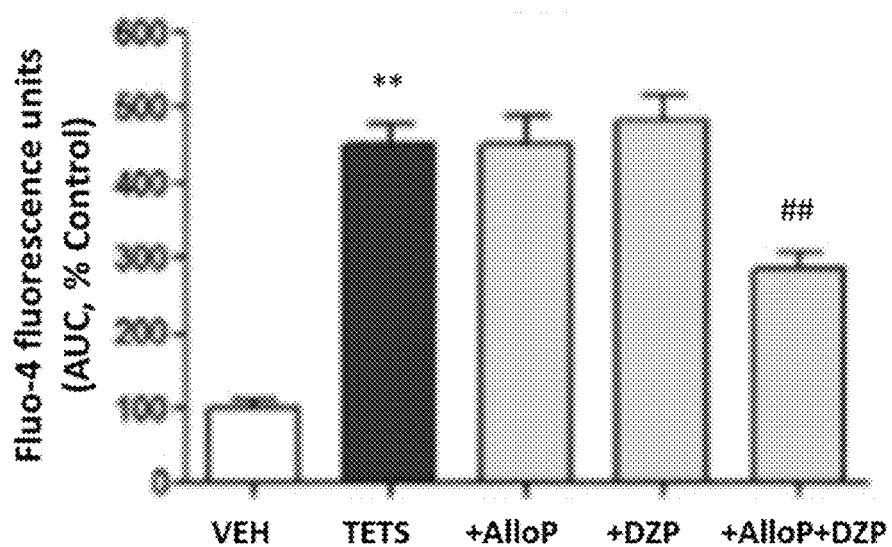
Figure 9C:
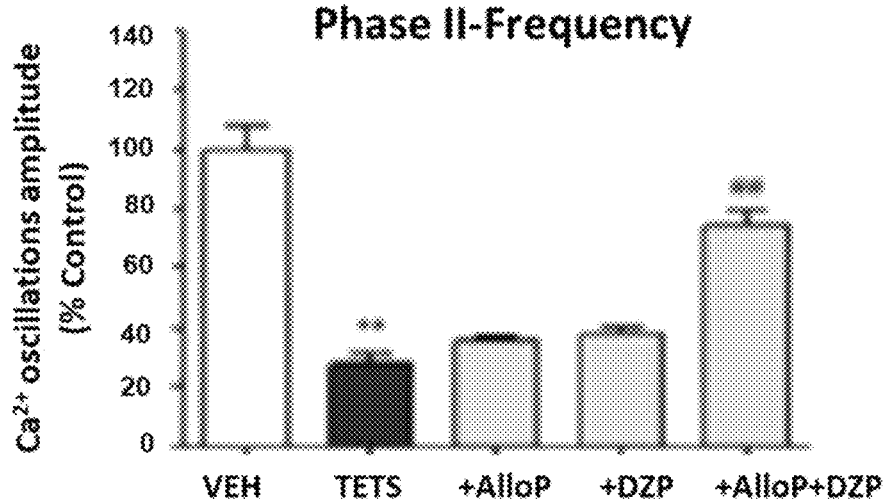
Figure 9D:
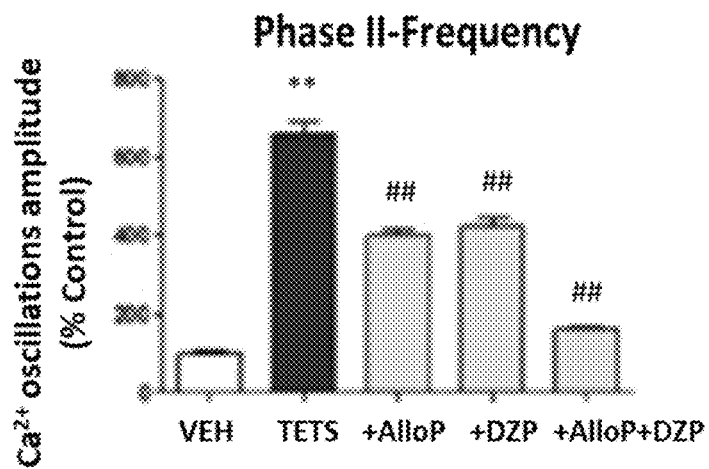

We next determined if the $GABA_A$ receptor positive modulators diazepam and allopregnanolone could protect against TETS-induced Ca2| dysregulation. FIG. 7A (top trace) demonstrates that the oscillatory activity of neurons exposed to vehicle remained stable over the entire recording period. Introduction of diazepam (0.1, 0.3, or 1 μM) caused an attenuation in the amplitude of basal spontaneous Ca2+ oscillations (FIG. 7A) Pre-exposure to diazepam caused a small concentration-dependent reduction of the Phase I integrated rise in Ca2+ induced by TETS that reached statistical significance only at 1 μM (FIG. 7B). Diazepam did not eliminate the Phase I plateau response (FIG. 7A). Diazepam also caused a partial inhibition of the Phase II frequency and amplitude effects of TETS, with the effect on amplitude reaching significance at 0.1 μM (FIG. 7C, D).

As shown in FIG. 8, allopregnanolone similarly attenuated the effects of TETS on Ca2| dysregulation. Allopregnanolone (0.1-1 μM) caused a concentration-dependent suppression of basal spontaneous Ca2· fluctuations and it partially attenuated the response in Phase I at 1 μM without eliminating the plateau in Ca2| levels (FIG. 8A, B). Allopregnanolone at 0.3 and 1 μM also inhibited the Phase II effect of TETS on frequency and amplitude with a completely reversed Phase II effect on amplitude at 1 μM (FIG. 8C,D).

Low Concentrations of Diazepam and Allopregnanolone in Combination Mitigate TETS-Induced Ca2· Dysregulation.

We next evaluated the effect of a combination of diazepam and allopregnanolone, each at a low concentration (0.1 μM) that by itself has minimal effects on Phase I or Phase II Ca2· dysregulation. As shown in FIG. 9, the combination they strongly mitigated both Phase I and Phase II effects. In fact, the combination treatment was able to largely eliminate the plateau response obtained with acute TETS exposure (FIG. 9A), an effect not obtained with 10-fold higher concentrations of diazepam (FIG. 7) or allopregnanolone (FIG. 8) alone.

Discussion

In the present study, we characterized the effects of TETS on hippocampal neurons in culture using MEA field potential recording and Fluo-4 fluorescence measurements of Ca2| dynamics in the neuronal network. Over time, hippocampal neurons in culture develop a rich network of processes and form numerous functional synaptic contacts (Mennerick et al., 1995; Arnold et al., 2005). Cultures that have developed for 13-17 DIV as used in the present study are well organized and there is robust spontaneous electrical activity mediated by excitatory and inhibitory transmission between neurons. Neurons within the cultures exhibit spontaneous action potentials and cultures of sufficient cell density may show synchronized bursting of neurons throughout the entire culture (Arnold et al., 2005). Excitatory synaptic transmission is mediated by functional glutamate receptors of the NMDA and AMPA types (Abele et al., 1990). Importantly, the cultures contain GABAergic neurons, comprising approximately 10 percent of the neurons, that form robust inhibitory synaptic connections mediated by $GABA_A$ receptors (Jensen et al., 1999; Jensen et al., 2000). Inhibitory synaptic potentials in hippocampal cultures have physiological properties that are similar to those obtained in intact preparations (Jensen et al., 1999) The GABAergic neurons impose tonic inhibition onto the network so that exposure of hippocampal cultures to $GABA_A$ receptor antagonists causes increased action potential firing, spontaneous rhythmic neuronal depolarizations, and bursting. The rhythmic depolarizations and bursting is dependent upon action potentials as it is eliminated by tetrodotoxin.

MEA recording allow the electrical activity of multiple neurons within the cultures to be monitored whereas FLIPR® Fluo-4 fluorescence measurements provide a dynamic assessment of aggregate intracellular Ca2| levels (Cao et al., 2010; Cao et al., 2012). Using these assays, we found that TETS dramatically increases intracellular Ca2· levels and alters Ca2| dynamics, initially causing an transient increase on the intracellular Ca2· concentration ([Ca2·] i) followed by a decrease on the Ca2· oscillations having bigger amplitude. Assessment of ongoing electric activity in the cultures with MEA recording showed an overall increase in discharge frequency and a change in the pattern of the discharges to clustering followed by periods of electrical silence. The actions of TETS on neuronal Ca2− dynamics and electrical discharge activity occur within the same concentration range, suggesting the two effects are mechanistically linked. TETS-induced changes on Ca2· dynamics and on electrical discharges are similar to those observed with the $GABA_A$ receptor antagonists bicuculline or picrotoxin (Arnold et al., 2005; Cao et al., 2012). Additionally, TETS modulation of Ca2· dynamics and spontaneous neuronal firing activity in a concentration-dependent manner with EC50 values of approximately 1-2 μM which is consistent with the affinity of TETS for $GABA_A$ receptors (Bowery et al., 1975; Dray, 1975, Roberts et al., 1981). Collectively these data support the view that the $GABA_A$ receptor blocking activity of TETS is responsible for the effects. Like picrotoxin, TETS is believed to be a reversible inhibitor of $GABA_A$ receptors, which is also consistent with the rapid reversibility of its effects in the MEA assay.

TETS-triggered alterations in electric firing and synchronous Ca2+ oscillations appear to rely on spontaneous action potentials since they are prevented by tetrodotoxin block of Na+ channels. The neuronal specificity of TETS in producing both Phase I and Phase II Ca2· responses in hippocampal cultures is also indicated by the observations that addition of TETS up to 3 μM to the culture medium of skeletal myotubes alters neither basal Ca2· homeostasis nor electrically evoked Ca2· transients (i.e., excitation-contraction coupling).

A key observation in the present study is that the alterations in Ca2| dynamics induced by TETS was largely inhibited by MK-801 demonstrating that NMDA receptors are required. While direct activation of NMDA receptors by TETS is not excluded, activation of NMDA receptors by bath application of NMDA increase the neuronal firing in a evenly distributed pattern which is not similar to the clustered bursts firng elicited by TETS or other $GABA_A$ receptors blocker/antagonist such as picrotoxin (Cao et al., 2012) The NMDA receptor dependence for TETS response to the Ca2− is consistent with earlier evidences in vivo that the NMDA receptor antagonist MK-801 inhibits picrotoxin or bicuculline-induced convulsion in mice (Obara, 1995; Czlonkowska et al., 2000) and ex vivo that the NMDA antagonist 2-APV suppresses picrotoxin-induced Ca2· responses as well as the frequency and duration of the epileptiform discharges in hippocampal slice preparation (Kohr and Heinemann, 1989). How the suppression of $GABA_A$ receptors activity by TETS affects NMDA receptor functions remains to be established. One possibility is that the Phase I [Ca2+]i response may involve presynaptic glutamate transmission. In support, bicuculline-induced [Ca2−]i responses have been shown to involve synaptic but not-extra-synaptic NMDA receptor activation (Hardingham et al., 2001; Hardingham et al., 2002). While the relationship between the Ca2| signals in the rapid throughput FLIPR assay and epileptic activity remain to be determined, our observation that NMDA receptors are required for the TETS-induced changes in Ca2· dynamics supports the concept that the effects on Ca2| are a surrogate for epileptic activity and may be useful as a model for therapeutics discovery. This is further supported by our demonstration that $GABA_A$ receptors positive allosterical enhancer, diazepam or allopregnanolone partially suppress TETS-induced modulation of Ca2+ dynamics.

Consistent with the role of $GABA_A$ receptors in restraining bursting and altered Ca2| dynamics is our observation that the $GABA_A$ receptor positive modulators diazepam and allopregnanolone are able to protect against the effects of TETS on Ca2+ dynamics. Allopregnanolone was more effective on mitigation of Phase I response induced by TETS than diazepam. This is consistent with the fact that diazepam only acts on synaptic $GABA_A$ receptors, whereas neurosteroids such as allopregnanolone can enhance both extrasynaptic synaptic $GABA_A$ receptors (Kokate et al., 1994; Lambert et al., 2003; Reddy and Rogawski, 2012). However, neither diazepam nor allopregnanolone alone was fully effective, even at the highest concentrations tested (1 µM). Unexpectedly, we found that the combination of diazepam and allopregnanolone, each at a threshold concentration of 0.1 µM, was highly effective at protecting against the effects of TETS on Ca2+ dynamics, causing a nearly complete inhibition of the Phase I response, including the plateau in Ca2−, as well as the Phase II changes. The combination of a benzodiazepine and a neurosteroid has not to our knowledge previously been studied in a simplified functional system. It is well recognized that benzodiazepines such as diazepam only act on synaptic $GABA_A$ receptors, whereas neurosteroids such as allopregnanolone preferentially enhance extrasynaptic $GABA_A$ receptors although they also act on synaptic receptors as well (Kokate et al., 1994; Lambert et al., 2003; Reddy and Rogawski, 2012). Without being bound to theory, it appears that the combined action on synaptic and extrasynaptic receptors accounts for the unique potency of the drug combination.

Alternatively, there may be an interaction at the level of individual $GABA_A$ receptors. The recognition sites for neurosteroids on $GABA_A$ receptors are distinct from those that recognize benzodiazepines and barbiturates (Johnston, 1996). It is conceivable, however, that allopregnanolone and diazepam could produce a synergistic enhancement of $GABA_A$ receptors in a similar fashion as the synergism that occurs between barbiturates and benzodiazepines, where there is known to be allosteric coupling (DeLorey et al., 1993).

In summary, we have developed rapid throughput methods to detect TETS-induced Ca2| dysregulation and altered electrical activity in cultured hippocampal neurons. We demonstrated that two $GABA_A$ receptors allosteric modulators, allopregnanolone and diazepam, when introduced singly prior to TETS, mitigate TETS-induced Ca2· dysregulation, demonstrating that the in vitro methods described here have translational value to identify new therapies and optimize combinatorial strategies for the prevention of TETS poisoning. The basic approaches described here are of general utility for investigating chemically diverse threat agents that elicit changes in the electrical behavior or Ca2− dynamics of in vitro neuronal networks. These rapid throughput approaches are useful for identifying novel targeted interventions and for optimizing therapeutic strategies involving drug combinations.

REFERENCES

Abele A E, Scholz K P, Scholz W K and Miller R J (1990) Excitotoxicity induced by enhanced excitatory neurotransmission in cultured hippocampal pyramidal neurons Neuron 4:413-419.

Arnold F J, Hofmann F, Bengtson C P, Wittmann M, Vanhoutte P and Bading H (2005) Microelectrode array recordings of cultured hippocampal networks reveal a simple model for transcription and protein synthesis-dependent plasticity. The Journal of physiology 564:3-19.

Banks C N, Rogawski M A, Yang D and P. J. L (2012) Tetramethylenedisulfotetramine. In: Encyclopedia of Toxicology, 3rd edition, volume 2 (Edited by P Wexler). Elsevier, Oxford, UK. In Press.

Barrueto F, Nelson L S, Hoffman R S, Heller M R, Furdyna P M, Hoffman R J, Whitlow K S, Belson M G and Henderson A K (2003) Poisoning by an illegally imported Chinese rodenticide containing tetramethylene-disulfotetramine—New York City, 2002 (Reprinted from MMWR, vol 52, pg 199-201, 2003). Jama-J Am Med Assoc 289: 2640-2642.

Bowery N G, Brown D A and Collins J F (1975) Tetramethylenedisulphotetramine: an inhibitor of gamma-aminobutyric acid induced depolarization of the isolated superior cervical ganglion of the rat. British journal of pharmacology 53:422-424.

Cao Z, Hulsizer S, Tassone F, Tang H T, Hagerman R J, Rogawski M A, Hagerman P J and Pessah I N (2012) Clustered Burst Firing in FMRI Premutation Hippocampal Neurons Amelioration with Allopregnanolone. Human molecular genetics 21:2923-2935.

Cao Z, LePage K T, Frederick M O, Nicolaou K C and Murray T F (2010) Involvement of caspase activation in azaspiracid-induced neurotoxicity in neocortical neurons. Toxicological sciences: an official journal of the Society of Toxicology 114:323-334.

Cao Z, Shafer T J and Murray T F (2011) Mechanisms of pyrethroid insecticide-induced stimulation of calcium influx in neocortical neurons. The Journal of pharmacology and experimental therapeutics 336: 197-205.

Casida J E, Eto M, Moscioni A D, Engel J L, Milbrath D S and Verkade J G (1976) Structure-Toxicity Relationships of 2,6,7-Trioxabicyclo[2.2.2]-Octanes and Related Compounds. Toxicology and applied pharmacology 36:261-279.

Choi H, Pereira A R, Cao Z, Shuman C F, Engene N, Byrum T, Matainaho T, Murray T F, Mangoni A and Gerwick W H (2010) The hoiamides, structurally intriguing neurotoxic lipopeptides from Papua New Guinea marine cyanobacteria. Journal of natural products 73:1411-1421.

Cole L M and Casida J E (1986) Polychlorocycloalkane insecticide-induced convulsions in mice in relation to disruption of the GABA-regulated chloride ionophore. Life sciences 39:1855-1862.

Croddy E (2004) Rat poison and food security in the People's Republic of China: focus on tetramethylene disulfotetramine (tetramine). Archives of toxicology 78:1-6.

Czlonkowska A I, Krzascik P, Sienkiewicz-Jarosz H, Siemiatkowski M, Szyndler J. Bidzinski A and Plaznik A (2000) The effects of neurosteroids on picrotoxin-, bicuculline- and NMDA-induced seizures, and a hypnotic effect of ethanol. Pharmacology, biochemistry, and behavior 67:345-353.

DeLorey T M, Kissin I, Brown P and Brown G B (1993) Barbiturate-benzodiazepine interactions at the gamma-aminobutyric acidA receptor in rat cerebral cortical synaptoneurosomes. Anesthesia and analgesia 77:598-605.

Deshpande L S, Carter D S, Blair R E and DeLorenzo R J (2010) Development of a prolonged calcium plateau in hippocampal neurons in rats surviving status epilepticus induced by the organophosphate diisopropylfluorophosphate. Toxicological sciences: an official journal of the Society of Toxicology 116:623-631.

Dray A (1975) Tetramethylenedisulphotetramine and amino acid inhibition in the rat brain. Neuropharmacology 14:703-705.

Esser T, Karu A E, Toia R F and Casida J E (1991) Recognition of tetramethylenedisulfotetramine and related sulfamides by the brain GABA-gated chloride channel and a cyclodiene-sensitive monoclonal antibody. Chemical research in toxicology 4:162-167.

Frega M, Pasquale V, Tedesco M, Marcoli M, Contestabile A, Nanni M, Bonzano L, Maura G and Chiappalone M (2012) Cortical cultures coupled to Micro-Electrode Arrays: a novel approach to perform in vitro excitotoxicity testing. Neurotoxicology and teratology 34:116-127.

Gerak L R, Stevenson M W, Winsauer P J and Moerschbaecher J M (2004) Effects of pregnanolone alone and in combination with other positive $GABA_A$ modulators on complex behavior in rats. Psychopharmacology 173: 195-202.

Guan F Y, Liu Y T, Luo Y, Hu X Y, Liu F, Li Q Y and Kang Z W (1993) GC/MS identification of tetramine in samples from human alimentary intoxication and evaluation of artificial carbonic kidneys for the treatment of the victims. Journal of analytical toxicology 17: 199-201.

Hardingham G E, Arnold F J and Bading H (2001) Nuclear calcium signaling controls CREB-mediated gene expression triggered by synaptic activity Nature neuroscience 4:261-267.

Hardingham G E, Fukunaga Y and Bading 11 (2002) Extrasynaptic NMDARs oppose synaptic NMDARs by triggering CREB shut-off and cell death pathways. Nature neuroscience 5:405-414.

Haskell A R and Voss F (1957) The Pharmacology of Tetramine (Tetraethylenedisulfotetramine). J Am Pharm Assoc 46:239-242.

Jensen K, Jensen M S, Bonefeld B E and Lambert J D (2000) Developmental increase in asynchronous GABA release in cultured hippocampal neurons. Neuroscience 101:581-588

Jensen K, Lambert J D and Jensen M S (1999) Activity-dependent depression of GABAergic IPSCs in cultured hippocampal neurons. Journal of neurophysiology 82: 42-49

Jett D A and Yeung D T (2010) The CounterACT Research Network: basic mechanisms and practical applications. Proceedings of the American Thoracic Society 7:254-256.

Jimbo Y, Robinson H P and Kawana A (1993) Simultaneous measurement of intracellular calcium and electrical activity from patterned neural networks in culture. IEEE transactions on bio-medical engineering 40:804-810.

Johnston G A (1996) $GABA_A$ receptor pharmacology. Pharmacology & therapcutics 69:173-198.

Johnstone A F, Gross G W, Weiss D G, Schroeder O H, Gramowski A and Shafer T J (2010) Microelectrode arrays a physiologically based neurotoxicity testing platform for the 21st century. Neurotoxicology 31:331-350

Kenet T, Froemke R C, Schreiner C E, Pessah I N and Merzenich M M (2007) Perinatal exposure to a noncoplanar polychlorinated biphenyl alters tonotopy, receptive fields, and plasticity in rat primary auditory cortex. Proceedings of the National Academy of Sciences of the United States of America 104: 7646-7651.

Kohr G and Heinemann U (1989) Effects of NMDA antagonists on picrotoxin-, low Mg2I- and low Ca2+-induced epileptogenesis and on evoked changes in extracellular Na+ and Ca2− concentrations in rat hippocampal slices. Epilepsy research 4:187-200.

Kokate T G, Svensson B E and Rogawski M A (1994) Anticonvulsant activity of neurosteroids: correlation with gamma-aminobutyric acid-evoked chloride current potentiation. The Journal of pharmacology and experimental therapeutics 270: 1223-1229.

Lambert J J, Belelli D, Peden D R, Vardy A W and Peters J A (2003) Neurosteroid modulation of $GABA_A$ receptors. Progress in neurobiology 71:67-80.

Li J M, Gan J, Zeng T F, Sander J W and Zhou (2011) Tetramethylenedisulfotetramine intoxication presenting with de novo Status Epilepticus: A case series. Neurotoxicology.

Mennerick S, Que J, Benz A and Zorumski C F (1995) Passive and synaptic properties of hippocampal neurons grown in microcultures and in mass cultures. Journal of neurophysiology 73:320-332.

Meyer D A, Carter J M, Johnstone A F and Shafer T J (2008) Pyrethroid modulation of spontaneous neuronal excitability and neurotransmission in hippocampal neurons in culture. Neurotoxicology 29:213-225.

Molina-Hernandez M, Tellez-Alcantara N P, Perez Garcia J, Olivera Lopez J I and Teresa Jaramillo M (2003) Anti-conflict-like actions of intralateral septal infusions of allopregnanolone in Wistar rats. Pharmacology, biochemistry, and behavior 75:397-404.

Obara N (1995) [Involvement of GABAergic and NMDA systems in drug-induced convulsions in mice] Nihon shinkei scishin yakurigaku zasshi=Japanese journal of psychopharmacology 15: 31-38.

Pereira A R, Cao Z, Engene N, Soria-Mercado I E, Murray T F and Gerwick W H (2010) Palmyrolide A, an unusually stabilized neuroactive macrolide from Palmyra Atoll cyanobacteria. Organic letters 12:4490-4493.

Ratra G S, Kamita S G and Casida J E (2001) Role of human GABA(A) receptor beta3 subunit in insecticide toxicity. Toxicology and applied pharmacology 172:233-240.

Reddy D S and Rogawski M A (2012) Neurosteroids—Endogenous regulators of seizure susceptibility and role in the treatment of epilepsy. Oxford University Press, In Press.

Roberts C J, James V A, Collins J F and Walker R J (1981) The action of seven convulsants as antagonists of the GABA response of Limulus neurons. Comparative biochemistry and physiology C: Comparative pharmacology 70:91-96.

Shafer T J, Rijal S O and Gross G W (2008) Complete inhibition of spontaneous activity in neuronal networks in vitro by deltamethrin and permethrin. Neurotoxicology 29: 203-212.

Soria-Mercado I F, Pereira A, Cao Z, Murray T F and Gerwick W H (2009) Alotamide A, a novel neuropharmacological agent from the marine cyanobacterium Lyngbya bouillonii Organic letters 11: 4704-4707.

Squires R F, Casida J F, Richardson M and Saederup E (1983) [35S]t-butylbicyclophosphorothionate binds with high affinity to brain-specific sites coupled to gamma-aminobutyric acid-A and ion recognition sites. Molecular pharmacology 23: 326-336.

Tanaka T, Saito H and Matsuki N (1996) Intracellular calcium oscillation in cultured rat hippocampal neurons: a model for glutamatergic neurotransmission. Japanese journal of pharmacology 70:89-93.

Voss E, Haskell A R and Gartenbe L (1961) Reduction of Tetramine Toxicity by Sedatives and Anticonvulsants. J Pharm Sci 50:858-&.

Wayman G A, Bose D D, Yang D, Lesiak A, Bruun D, Impey S, Ledoux V, Pessah I N and Lein P J (2012) PCB 95 Modulates Calcium-Dependent Signaling Pathway Responsible for Activity-Dependent Dendritic Growth. Environmental health perspectives.

Wayman G A, Lee Y S, Tokumitsu H, Silva A J and Soderling T R (2008) Calmodulin-kinases: modulators of neuronal development and plasticity Neuron 59:914-931.

Whitlow K S, Belson M, Barrueto F, Nelson L and Henderson A K (2005) Tetramethylenedisulfotetramine: old agent and new terror. Annals of emergency medicine 45: 609-613.

Wu Y Q and Sun C Y (2004) Poison control services in China. Toxicology 198:279-284.

Zhang Y, Su M and Tian D P (2011) Tetramine poisoning A case report and review of the literature Forensic science international 204:e24-27.

Zolkowska D, Banks C N, Dhir A, Inceoglu B, Sanborn J R, McCoy M R, Bruun D A, Hammock B D, Lein P J and Rogawski M A (2012) Characterization of seizures induced by acute and repeated exposure to tetramethylenedisulfotetramine. The Journal of pharmacology and experimental therapeutics 341: 435-446.

Example 2

Combination Treatment with a Benzodiazepine and a Neurosteroid Mitigates the Severity and Prevents the Lethality of Seizures Even when Administering after Seizure has Started In cultured hippocampal neurons, higher concentration of TETS (>3 µM) produces an acute elevation of intracellular Ca2| levels (Phase I response) and a prolonged Ca2· response with increased Ca2· oscillation amplitude and decreased frequency of the Ca2· oscillations (Phase II response). Both Phase I and Phase II response can be mitigated by the pretreatment of diazepam and allopregnanolone. More importantly, pre-treatment with a combination of low concentrations of diazepam and allopregnanolone, which have minimal effect against TETS-induced Ca2+ response, normalized the TETS Ca2+ response to the control level (Cao et al., Toxicological Sciences, 130: 362-372). In this study, we examined whether post-treatment (after TETS triggers Phase I and Phase II Ca2· responses) of neurons with diazepam and/or allopregnanolone mitigate alterations triggered by TETS, which is more relevant to the TETS poising. Since addition of TETS induces acute phase I response, we therefore only focused on the TETS-induced Phase II response. Addition of vehicle (0.1% DMSO) was no effect on the Ca2| dynamics over the recording period of 45 min. However, a concentration of 3 µM of TETS produced an acute Phase I and a prolonged Phase II effect, as previously reported (Cao et al 2012) While addition of diazepam (0.1 µM) or allopregnanolone (0.1 µM) singly was without significant effect on TETS-induced decreased Ca2+ oscillation frequency, diazepam (0.1 µM) and allopregnanolone (0.1 µM) in combination effectively recovered synchronous Ca2| oscillations characteristics comparable to those observed with vehicle-treated cultures. Although allopregnanolone (0.1 µM) alone decreased the TETS-induced Ca2· oscillation amplitude ~20% (p<0.01), the post-TETS treatment with diazepam (0.1 µM) and allopregnanolone (0.1 µM) in combination conferred much greater recovery of Ca2-oscillation amplitude to that below vehicle control, and occurred rapidly after the addition of diazepam and allopregnanolone (FIG. 10). These data clearly demonstrate that diazepam in combination with a neurosteroid, such as allopregnanolone, act in a synergistic manner to mitigate the severity of seizures and prevent the lethality of seizurogenic agents After the seizures have already started.

Example 3

In Vivo Assay Demonstrating the Therapeutic Efficacy of Combined Benzodiazepine and Neurosteroid in Mitigating TETS-Induced Seizures and Death When administered to adult male NIII Swiss mice at lethal doses, TETS typically causes two clonic seizures within the first 20 minutes after TETS injection with each seizure lasting approximately 30 to 45 seconds. These clonic seizures are followed by a tonic seizure that results in the death of >95% of the TETS-intoxicated animals (FIG. 11). Mice can be rescued from TETS-induced death if they are administered a very high dose of diazepam (5 mg/kg, i.p.) immediately following the second clonic seizure (FIG. 11). Administration of diazepam at 0.03 mg/kg immediately following the second clonic seizure protected <10% of the TETS-intoxicated animals from death (FIG. 12). Pretreatment with diazepam (0.1 mg/kg 10 minutes before TETS injection) protected <30% of the TETS-intoxicated animals from death (FIG. 13) Post-administration of the neurosteroid allopregnanolone at 0.03 mg/kg was no more efficacious than low dose diazepam in protecting TETS-intoxicated animals from death (FIG. 12). Pretreatment with allopregnanolone at 0.1 mg/kg protected ~50% of the TETS-intoxicated animals (FIG. 13). When administered simultaneously, the subthreshold doses of diazepam and allopregnanolone significantly increased survival of TETS-intoxicated animals. When administered immediately after the second clonic seizure, this benzodiazepine and neurosteroid combination, 100% of the TETS-intoxicated animals survived (FIG. 12). Used as a pretreatment, this combinatorial therapy protected ~75% of the TETS-intoxicated animals (FIG. 13). Importantly, the therapeutic combination of subthreshold diazepam and allopregnanolone had no effect on blood pressure, whereas the dose of diazepam required to prevent TETS-induced tonic seizures and death when administered singly caused significant hypotension (FIG. 14).

The significance of these in vivo data are 3-fold: (1) these data confirm the predictive value of the in vitro screening system; (2) these data demonstrate that combinatorial therapy with a benzodiazepine and a neurosteroid, at subthreshold doses that singly have no effect, is efficacious in preventing seizures and in the case of TETS, in preventing death associated with tonic seizures; and (3) the combinatorial therapy avoids an important off-target adverse effect (significant decrease in blood pressure) associated with use of diazepam when used singly at therapeutic doses.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of preventing or mitigating a seizure in a subject in need thereof, comprising:
   (a) determining that a subject is at risk of being exposed to a nerve agent or pesticide that can cause seizures, and
   (b) administering to the subject of an effective amount of a benzodiazepine and allopregnanolone, wherein each of the benzodiazepine and the allopregnanolone are administered in a subtherapeutic dose, and wherein the subtherapeutic dose of the benzodiazepine is in the range of 0.3 µg/kg to 3.0 µg/kg.

2. The method of claim 1, wherein the agent or pesticide is an organophosphorus nerve agent or pesticide.

3. The method of claim 1, wherein the nerve agent or pesticide is selected from the group consisting of tabun, sarin, soman, GF, VR, VX, Acephate (Orthene), Azinphosmethyl (Gusathion, Guthion), Bensulide (Betasan, Lescosan), Bomyl (Swat), Bromophos (Nexion), Bromophosethyl (Nexagan), Cadusafos (Apache, Ebufos, Rugby), Carbophenothion (Trithion), Chlorethoxyfos (Fortress), Chlorfenvinphos (Apachlor, Birlane), Chlormephos (Dotan), Chlorphoxim (Baythion-C), Chlorpyrifos (Brodan, Dursban, Lorsban), Chlorthiophos (Celathion), Coumaphos (Asuntol, Co-Ral), Crotoxyphos (Ciodrin, Cypona), Crufomate (Ruelene), Cyanofenphos (Surecide), Cyanophos (Cyanox), Cythioate (Cyflee, Proban), DEF (De-Green), Demeton (Systox), Demeton-S-methyl (Duratox, Metasystoxl), Dialifor (Torak), Diazinon, Dichlorofenthion, (VC-13 Nemacide), Dichlorvos (DDVP, Vapona), Dicrotophos (Bidrin), Dimefos (Hanane, Pestox XIV), Dimethoate (Cygon, DeFend), Dioxathion (Delnav), Disulfoton (Disyston), Ditalimfos, Edifenphos, Endothion, EPBP (S-seven), EPN, Ethion (Ethanox), Ethoprop (Mocap), Ethyl parathion (E605, Parathion, thiophos), Etrimfos (Ekamet), Famphur (Bash, Bo-Ana, Famfos), Fenamiphos (Nemacur), Fenitrothion (Accothion, Agrothion, Sumithion), Fenophosphon (Agritox, trichloronate), Fensulfothion (Dasanit), Fenthion (Baytex, Entex, Tiguvon), Fonofos (Dyfonate, N-2790), Formothion (Anthio), Fosthietan (Nem-A-Tak), Heptenophos (Hostaquick), Hiometon (Ekatin), Hosalone (Zolone), IBP (Kitazin), Iodofenphos (Nuvanol-N), Isazofos (Brace, Miral, Triumph), Isofenphos (Amaze, Oftanol), Isoxathion (E-48, Karphos), Leptophos (Phosvel), Malathion (Cythion), Mephosfolan (Cytrolane), Merphos (Easy Off-D, Folex), Methamidophos (Monitor), Methidathion (Supracide, Ultracide), Methyl parathion (E601, Penncap-M), Methyl trithion, Mevinphos (Duraphos, Phosdrin), Mipafox (Isopestox, Pestox XV), Monocrotophos (Azodrin), Naled (Dibrome), Oxydemeton-methyl (Metasystox-R), Oxydeprofos (Metasystox-S), Phencapton (G 28029), Phenthoate (Dimephenthoate, Phenthoate), Phorate (Rampart, Thimet), Phosalone (Azofene, Zolone), Phosfolan (Cylan, Cyolane), Phosmet (Imidan, Prolate), Phosphamidon (Dimecron), Phostebupirim (Aztec), Phoxim (Baythion), Pirimiphos-ethyl (Primicid), Pirimiphos-methyl (Actellic), Profenofos (Curacron), Propetamphos (Safrotin), Propyl thiopyrophosphate (Aspon), Prothoate (Fac), Pyrazophos (Afugan, Curamil), Pyridaphenthion (Ofunack), Quinalphos (Bayrusil), Ronnel (Fenchlorphos, Korlan), Schradan (OMPA), Sulfotep (Bladafum, Dithione, Thiotepp), Sulprofos (Bolstar, Helothion), Temephos (Abate, Abathion), Terbufos (Contraven, Counter), Tetrachlorvinphos (Gardona, Rabon), Tetraethyl pyrophosphate (TEPP), tetramethylenedisulfotetramine (TETS), Triazophos (Hostathion), and Trichlorfon (Dipterex, Dylox, Neguvon, Proxol).

4. The method of claim 1, wherein the nerve agent or pesticide is tetramethylenedisulfotetramine (TETS).

5. The method of claim 1, wherein the benzodiazepine and the allopregnanolone are co-administered together and/or by the same route of administration.

6. The method claim 1, wherein the benzodiazepine and the allopregnanolone are co-administered separately and/or by different routes of administration.

7. The method claim 1, wherein one or both of the benzodiazepine and the allopregnanolone are administered by the inhalational or intrapulmonary route of administration.

8. The method of claim 7, wherein the benzodiazepine and the allopregnanolone are not heated prior to administration.

9. The method of claim 7 or 8, wherein one or both of the benzodiazepine and allopregnanolone are aerosolized.

10. The method claim 9, wherein one or both of the benzodiazepine and the allopregnanolone aerosolized particulates having a mass median aerodynamic diameter ranging from about 1µm to about 3µm.

11. The method of claim 1, wherein the allopregnanolone is administered at a dose in the range of about 5 mg/kg to about 50 mg/kg.

12. The method of claim 1, wherein the benzodiazepine is selected from the group consisting of bretazenil, clonazepam, cloxazolam, clorazepate, diazepam, fludiazepam, flutoprazepam, lorazepam, midazolam, nimetazepam, nitrazepam, phenazepam, temazepam and clobazam.

13. The method of claim 1, further comprising the co-administration of an NMDA receptor antagonist.

14. The method of claim 13, wherein the NMDA receptor antagonist is selected from the group consisting of dizocilpine (MK-801), meperidine, methadone, dextropropoxyphene, tramadol, ketobemidone, ketamine, dextromethorphan, phencyclidine, nitrous oxide ($N_2O$), APS (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), selfotel, amantadine, dextrallorphan, dextrorphan, ethanol, eticyclidine, gacyclidine, ibogaine, magnesium, memantine, methoxetamine, rolicyclidine.tenocyclidine, methoxydine, tiletamine, xenon, neramexane, eliprodil, etoxadrol, dexoxadrol, WMS 2539, NEFA, remacemide, delucemine, 8A-PDHQ, aptiganel, HU-211, rhynchophylline, 1-Aminocyclopropanecarboxylic acid (ACPC), 7-Chlorokynurenate, DCKA (5,7-dichlorokynurenic acid), kynurenic acid, lacosamide, CP-101,606 (traxoprodil), AZD6765 (lanicemine) and GLYX-13.

16. The method of claim 13, wherein the benzodiazepine, allopregnanolone and NMDA receptor antagonist are co-administered together and/or by the same route of administration.

16. The method of claim 13, wherein the benzodiazepine, allopregnanolone and NMDA receptor antagonist are administered separately and/or by different routes of administration.

* * * * *